US006855811B2

(12) United States Patent
Bandman et al.

(10) Patent No.: US 6,855,811 B2
(45) Date of Patent: Feb. 15, 2005

(54) HUMAN PROTEASE MOLECULES

(75) Inventors: Olga Bandman, Mountain View, CA (US); Jennifer L. Hillman, Mountain View, CA (US); Henry Yue, Sunnyvale, CA (US); Karl J. Guegler, Menlo Park, CA (US); Neil C. Corley, Mountain View, CA (US); Y. Tom Tang, Sunnyvale, CA (US); Purvi Shah, Sunnyvale, CA (US)

(73) Assignee: Incyte Pharmaceuticals, Inc., Palo Alto, CA (US)

(*) Notice: Subject to any disclaimer, the term of this patent is extended or adjusted under 35 U.S.C. 154(b) by 0 days.

(21) Appl. No.: 09/968,415

(22) Filed: Sep. 26, 2001

(65) Prior Publication Data

US 2002/0086334 A1 Jul. 4, 2002

Related U.S. Application Data

(62) Division of application No. 09/659,151, filed on Sep. 11, 2000, which is a division of application No. 09/008,271, filed on Jan. 16, 1998, now Pat. No. 6,203,979.

(51) Int. Cl.$^7$ ............................ C07K 16/40; C12Q 1/37

(52) U.S. Cl. ...................................... 530/387.9; 435/7.4

(58) Field of Search ......................... 530/387.9; 435/7.4

(56) References Cited

U.S. PATENT DOCUMENTS

| 2,930,736 | A | | 3/1960 | Sullivei ........................ 167/73 |
| 4,499,014 | A | * | 2/1985 | Estis ............................ 260/112 |
| 4,558,005 | A | * | 12/1985 | Goldwasser et al. ........... 435/7 |

FOREIGN PATENT DOCUMENTS

| EP | 198645 A | 11/1990 |
| WO | WO 98/11236 | 3/1998 |
| WO | WO 98/21328 | 5/1998 |
| WO | WO 98/22597 | 5/1998 |
| WO | WO 98/39448 | 11/1998 |
| WO | WO 98/56804 | 12/1998 |
| WO | WO 99/09138 | 2/1999 |
| WO | WO 99/14328 | 3/1999 |
| WO | WO 99/46281 | 9/1999 |
| WO | WO 00/12708 | 3/2000 |

OTHER PUBLICATIONS

Hamilton, S.R. (1984) Scand. J. Gastroenterol. Suppl. 93, 13–23.*
Madara, J.L. (1999) Textbook of Gastroenterology, erd Ed., Yamada, et al. Ed., Lipincott, pp. 141–142.*
Goldberg, D.M., et al. (1969) Enzymologia 36(4–5), 227–238.*
Katunuma, N. et la., "Studies on New Intracellular Proteases in Various Organs of Rat", Eur. J. Biochem., 52–37–50 (1975).

Yasuda, Y. et al., "Characterization of new fluorogenic substrates for the rapid and sensitive assay of cathepsin E and cathepsin D", J. Biochem., 125(6):1137–43 (Jun. 1999) (Abstract only).
L. Hillier et al., "WashU–NCI human EST Project," (EMBL database, accession No. AA143709), Dec. 14, 1996.
R. Strausberg, "National Cancer Institute, Cancer Genome Anatomy Project . . . ," (EMBL database, accession No. AA641005), Nov. 1, 1997.
"Blast 2 Sequences Results"—Exhibits A–O, NCBI, http:// www.ncbi.nlm.nih.gov/blast/b12seq/wblast2.cgi?2, (Aug. 27, 2003).
Yousef, G. et al., "The New Human Tissue Kalikrein Gene Family: Structure, Function, and Association to Disease", Endocrine Reviews, 22(2):184–204 (2001).
Harvey, T.J. et al., (Direct Submission), GenBank Sequence Database (Accession No. 071329), National Center for Biotechnology Information, National Library of Medicine, Bethesda, Maryland 20894 (GI: 11545747) (Apr. 16, 2002).
Rieder, J.J. et al., (Direct Submission), GenBank Sequence Database (Accession No. AAM11874), National Center for Biotechnology Information, National Library of Medicine, Bethesda, Maryland 20894 (GI:20160213) (Apr. 15, 2002).
Clustal W Results, Multiple Sequence Alignments, (G11545747) (Apr. 23, 2002).
Clustal W Results, Multiple Sequence Alignments (G20160213) (Apr. 23, 2002).
Tatnell, P.J. et al., "Napsins: new human aspartic proteinases", FEBS Letters, 441:43–48 (1998).
Koelsch, G. et al., "New human aspartic proteases napsin 1 and napsin 2: Molecular cloning and intracellular localization of napsin 1", Database EMHUM1 (Online) EMBL, Accession No. AF098485, Feb. 8, 1999.
Beynon, R.J. and J.S. Bond, Proteolytic Enzymes: A Practical Approach, Oxford University Press, New York, NY, pp. 1–5 (1994).
von Heijne, G., "A new method for predicting signal sequence cleavage sites", Nuc. Acid. Res., 14: 4683–4690 (1986).
Zunino, S. J. et al., "RNKP–1, a Novel Natural Killer–Associated Serine Protease Gene Cloned from RNK–16 Cytotoxic Lymphocytes", J. Immunol., 144: 2001–2009 (1990).
Sayers, T.J. et al., "Purification and Cloning of a Novel Serine Protease, RNK–Tryp–1, from the Granules of a Rat NK Cell Leukemia", J. Immunol., 152: 2289–2297 (1994).
Keyszer, G.M. et al., "Comparative Analysis of Cathepsin L, Cathepsin D, and Collagenase Messenger RNA Expression in Synovial Tissues of Patients with Rheumatoid Arthritis and Osteoarthritis, by in Situ Hybridization", Arthritis Rheum., 38: 976–984 (1995).

(List continued on next page.)

Primary Examiner—Charles L. Patterson, Jr.
(74) Attorney, Agent, or Firm—Merchant & Gould

(57) ABSTRACT

The invention provides human protease molecules (HUPM) and polynucleotides which identify and encode HUPM. The invention also provides expression vectors, host cells, antibodies, agonists, and antagonists. The invention also provides methods for treating or preventing disorders associated with expression of HUPM.

27 Claims, No Drawings

OTHER PUBLICATIONS

Chambers, A.F. and A.B. Tuck, "Ras–Responsive Genes and Tumor Metastasis", *Crit. Rev. Oncog.,* 4: 95–114 (1993).

Cuypers, H.T. et al., "Sulfhydryl Content of Bovine Eye Lens Leucine Aminopeptidase", *J. Biol. Chem.,* 257: 7086–7091 (1982).

Shelness, G.S. and G. Blobel, "Two Subunits of the Canine Signal Peptidase Complex Are Homologous to Yeast SEC11 Protein", *J. Biol. Chem.,* 265: 9512–9519 (1990).

Ciechanover, A., "The Ubiquitin–Proteasome Proteolytic Pathway", *Cell,* 79: 13–21 (1994).

Murphy, G., "The Regulation of Connective Tissue Metalloproteinases by Natural Inhibitors", *Agents Actions Suppl.,* 35: 69–76 (1991).

Calkins, C.C. and B.F. Sloane, "Mammaliam Cysteine Protease Inhibitors: Biochemical Properties and Possible Roles in Tumor Progression", *Biol. Biochem. Hoppe Seyler,* 376: 71–80 (1995).

Tanaka, K. et al., (Direct Submission), GenBank Sequence Database (Accession M58593), National Center for Biotechnology Information, National Library of Medicine, Bethesda, Maryland, 20894 (GI 203206; GI 203207) (1993).

Tanaka, K. et al., (Direct Submission), GenBank Sequence Database (Accession 203207), National Center for Biotechnology Information, National Library of Medicine, Bethesda, Maryland, 20894 (GI 203207) (1992).

Tsurumi, C. et al., (Direct Submission), GenBank Sequence Database (Accession D50063), National Center for Biotechnology Information, National Library of Medicine, Bethesda, Maryland, 20894 (GI 971269; GI 971270) (1996).

Tsurumi, C. et al., (Direct Submission), GenBank Sequence Database (Accession 971270), National Center for Biotechnology Information, National Library of Medicine, Bethesda, Maryland, 20894 (GI 971270) (1996).

Brown, J. et al., (GI 2582045), GenBank Sequence Database (Accession AAB82449), National Center for Biotechnology Information, National Library of Medicine, Bethesda, Maryland 20894, Nov. 2, 1997.

Geneseq Report of Relevant Sequence in JP62000276–A: ID: N71123; Apr. 19, 1991.

SWISS–PROT: P56202, Release 35, Nov. 1997.

Katunuma, N. et al., *J. Biochem.,* 83:625–628 (1978).

Chao, J. et al., *Biochem. Biophys. Res. Comm.,* 121 (2) : 722–729 (1984).

* cited by examiner

HUMAN PROTEASE MOLECULES

This application is a divisional application of U.S. application Ser. No. 09/659,151, filed Sep. 11, 2000, which application is a divisional application of U.S. Ser. No. 09/008,271, filed Jan. 16, 1998, and issued on Mar. 20, 2001 as U.S. Pat. No. 6,203,979, all of which application and patents are hereby incorporated herein by reference.

FIELD OF THE INVENTION

This invention relates to nucleic acid and amino acid sequences of human protease molecules and to the use of these sequences in the diagnosis, treatment, and prevention of cell proliferative and immune disorders.

BACKGROUND OF THE INVENTION

Proteolytic processing is an essential component of normal cell growth, differentiation, remodeling, and homeostasis. The cleavage of peptide bonds within cells is necessary for the maturation of precursor proteins to their active form, the removal of signal sequences from targeted proteins, the degradation of incorrectly folded proteins, and the controlled turnover of peptides within the cell. Proteases participate in apoptosis, inflammation, and in tissue remodeling during embryonic development, wound healing, and normal growth. They are necessary components of bacterial, parasitic, and viral invasion and replication within a host. Four principal categories of mammalian proteases have been identified based on active site structure, mechanism of action, and overall three-dimensional structure. (Beynon, R. J. and J. S. Bond (1994) *Proteolytic Enzymes: A Practical Approach*, Oxford University Press, New York, N.Y., pp. 1–5.)

The serine proteases (SPs) are a large family of proteolytic enzymes that include the digestive enzymes, trypsin and chymotrypsin; components of the complement cascade and of the blood-clotting cascade; and enzymes that control the degradation and turnover of macromolecules of the extracellular matrix. SPs are so named because of the presence of a serine residue found in the active catalytic site for protein cleavage and usually within the sequence GDSGGP. The active site of all SP is composed of a triad of residues including the aforementioned serine, an aspartate, and a histidine residue. SPs have a wide range of substrate specificities and can be subdivided into subfamilies on the basis of these specificities. The main sub-families are trypases which cleave after arginine or lysine; aspases which cleave after aspartate; chymases which cleave after phenylalanine or leucine; metases which cleavage after methionine; and serases which cleave after serine.

The SPs are secretory proteins containing N-terminal signal peptides which export the immature protein across the endoplasmic reticulum prior to cleavage. (von Heijne, G. (1986) Nuc. Acid. Res. 14:5683–5690). Differences in these signal sequences provide one means of distinguishing individual SPs. Some SPs, particularly the digestive enzymes, exist as inactive precursors or preproenzymes and contain a leader or activation peptide on the C-terminal side of the signal peptide. This activation peptide may be 2–12 amino acids in length, and extend from the cleavage site of the signal peptide to the N-terminus of the active, mature protein. Cleavage of this sequence activates the enzyme. This sequence varies in different SPs according to the biochemical pathway and/or its substrate. (Zunino, S. J. et al. (1990) J. Immunol. 144:2001–2009; and Sayers, T. J. et al. (1994) J. Immunol. 152:2289–2297.)

Cysteine proteases are involved in diverse cellular processes ranging from the processing of precursor proteins to intracellular degradation. Mammalian cysteine proteases include lysosomal cathepsins and cytosolic calcium activated proteases, calpains. Cysteine proteases are produced by monocytes, macrophages and other cells of the immune system which migrate to sites of inflammation and in their protective role secrete various molecules to repair damaged tissue. These cells may overproduce the same molecules and cause tissue destruction in certain disorders. In autoimmune diseases such as rheumatoid arthritis, the secretion of the cysteine protease, cathepsin C, degrades collagen, laminin, elastin and other structural proteins found in the extracellular matrix of bones. The cathepsin family of lysosomal proteases includes the cysteine proteases; cathepsins B, H, K, L, O2, and S; and the aspartyl proteases; cathepsins D and G. Various members of this endosomal protease family are differentially expressed. Some, such as cathepsin D, have a ubiquitous tissue distribution while others, such as cathepsin L, are found only in monocytes, macrophages, and other cells of the immune system.

Abnormal regulation and expression of cathepsins is evident in various inflammatory disease states. In cells isolated from inflamed synovia, the mRNA for stromelysin, cytokines, TIMP-1, cathepsin, gelatinase, and other molecules is preferentially expressed. Expression of cathepsins L and D is elevated in synovial tissues from patients with rheumatoid arthritis and osteoarthritis. Cathepsin L expression may also contribute to the influx of mononuclear cells which exacerbates the destruction of the rheumatoid synovium. (Keyszer, G. M. (1995) Arthritis Rheum. 38:976–984.) The increased expression and differential regulation of the cathepsins is linked to the metastatic potential of a variety of cancers and as such is of therapeutic and prognostic interest. (Chambers. A. F. et al. (1993) Crit. Rev. Oncog. 4:95–114.)

Cysteine proteases are characterized by a catalytic domain containing a triad of amino acid residues similar to that found in serine proteases. A cysteine replaces the active serine residue. Catalysis proceeds via a thiol ester intermediate and is facilitated by the side chains of the adjacent histidine and aspartate residues.

Aspartic proteases include bacterial penicillopepsin, mammalian pepsin, renin, chymosin, and certain fungal proteases. The characteristic active site residues of aspartic proteases are a pair of aspartic acid residues, e.g., asp33 and asp213 in penicillopepsin. Aspartic proteases are also called acid proteases because the optimum pH for activity is between 2 and 3. In this pH range, one of the aspartate residues is ionized, the other un-ionized. A potent inhibitor of aspartic proteases is the hexapeptide, pepstatin, which in the transition state resembles normal substrates.

Carboxypeptidases A and B are the principal mammalian representatives of the metallo-protease family. Both are exopeptidases of similar structure and active sites. Carboxypeptidase A, like chymotrypsin, prefers C-terminal aromatic and aliphatic side chains of hydrophobic nature, whereas carboxypeptidase B is directed toward basic arginine and lysine residues. Active site components include zinc, with its three ligands of two glutamic acid and one histidine residues.

Many other proteolytic enzymes do not fit any of the major categories discussed above because their mechanisms of action and/or active sites have not been elucidated. These include the aminopeptidases and signal peptidases.

Aminopeptidases catalyze the hydrolysis of amino acid residues from the amino terminus of peptide substrates.

Bovine leucine aminopeptidase is a zinc metallo-enzyme that utilizes the sulfydryl groups from at least three reactive cysteine residues at its active site in the binding of metal ions. (Cuypers, H. T. et al. (1982) J. Biol. Chem. 257:7086–7091.)

Signal peptidases are a specialized class of proteases found in all prokaryotic and eukaryotic cell types that serve in the processing of signal peptides from certain proteins. Signal peptides are amino-terminal sequences on a protein which directs the protein from its ribosomal assembly site to a particular cellular or extracellular location. Once the protein has been exported, removal of the signal sequence by a signal peptidase and posttranslational processing, e.g., glycosylation or phosphorylation, activate the protein. Signal peptidases exist as multi-subunit complexes in both yeast and mammals. The canine signal peptidase complex is composed of five subunits; all associate with the mitochondrial membrane, and containing hydrophobic regions that span the membrane one or more times. (Shelness, G. S. and Blobel, G. (1990) J. Biol. Chem. 265:9512–9519.) Some of these subunits serve to fix the complex in its proper position on the membrane while others contain the actual catalytic activity. The catalytic activity appears to involve a serine residue in its active site.

Proteasome is an intracellular protease complex which is found in some bacteria and in all eukaryotic cells and plays an important role in cellular physiology. Proteasomes are responsible for the timely degradation of cellular proteins of all types and control proteins that function to activate or repress cellular processes such as transcription and cell cycle progression. (Ciechanover, A. (1994) Cell 79:13–21.) Proteasomes act on proteins which have been targeted for hydrolysis by the covalent attachment of a small protein called ubiquitin to lysine side chains of the protein. Ubiquitin-proteasome systems are implicated in the degradation of mitotic cyclic kinases, oncoproteins, tumor suppressor genes (p53), cell surface receptors associated with signal transduction, transcriptional regulators, and mutated or damaged proteins. (Ciechanover, supra.) Proteasomes are large (~2000 kDa), multisubunit complexes composed of a central catalytic core containing a variety of proteases and terminal subunits that serve in substrate recognition and regulation of proteasome activity.

Protease inhibitors play a major role in the regulation of the activity and effect of proteases. They have been shown to control pathogenesis in animal models of proteolytic disorders. (Murphy, G. (1991) Agents Actions Suppl 35:69–76.) In particular, low levels of the cystatins, low molecular weight inhibitors of the cysteine proteases, seem to be correlated with malignant progression of tumors. (Calkins, C. et al (1995) Biol Biochem Hoppe Seyler 376:71–80.) The balance between levels of cysteine proteases and their inhibitors is also significant in the development of disorders. Specifically, increases in cysteine protease levels, when accompanied by reductions in inhibitor activity, are correlated with increased malignant properties of tumor cells and the pathology of arthritis and immunological diseases in humans.

The serpins are high molecular weight, e.g., 370–420 amino acid residues, inhibitors of mammalian plasma serine proteases. Many of these inhibitors serve to regulate the blood clotting cascade and/or the complement cascade in mammals. Prominent among these inhibitors are α-1 protease inhibitor, α-1-antichymotrypsin, antithrombin III, and the "universal protease inhibitor" α-2 macroglobulin. α-1 protease inhibitor is primarily effective against the neutrophil elastase but combines with other serine proteases as well. α-1 protease inhibitor, α-1-antichymotrypsin, and antithrombin III all show striking sequence homology, suggesting that specialization of these inhibitors has occurred in response to specialization of the corresponding proteases themselves.

The discovery of new human protease molecules and the polynucleotides encoding them satisfies a need in the art by providing new compositions which are useful in the diagnosis, treatment, and prevention of cell proliferative and immune disorders.

SUMMARY OF THE INVENTION

The invention features substantially purified polypeptides, human protease molecules, referred to collectively as "HUPM" and individually as "HUPM-1", "HUPM-2", "HUPM-3", "HUPM-4", "HUPM-5", "HUPM-6", "HUPM-7", "HUPM-8", "HUPM-9", "HUPM-10", "HUPM-11", and "HUPM-12". In one aspect, the invention provides a substantially purified polypeptide, HUPM, comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, and fragments thereof.

The invention further provides a substantially purified variant of HUPM having at least 90% amino acid identity to the amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or to a fragment of any of these sequences. The invention also provides an isolated and purified polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, and fragments thereof. The invention also includes an isolated and purified polynucleotide variant having at least 90% polynucleotide identity to the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, and fragments thereof.

Additionally, the invention provides a composition comprising a polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, and fragments thereof. The invention further provides an isolated and purified polynucleotide sequence which hybridizes under stringent conditions to the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, and fragments thereof, as well as an isolated and purified polynucleotide sequence which is complementary to the polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, and fragments thereof The invention also provides an isolated and purified polynucleotide comprising a polynucleotide sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24. The invention further provides an isolated and purified polynucleotide variant having at least 90% polynucleotide identity to the polynucleotide comprising a polynucleotide sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24, and fragments thereof, as well as an isolated and purified polynucleotide which is complementary to the polynucleotide comprising a polynucleotide sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24, and fragments thereof.

The invention further provides an expression vector containing at least a fragment of the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, and fragments thereof. In another aspect, the expression vector is contained within a host cell.

The invention also provides a method for producing a polypeptide comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12, or fragments thereof, the method comprising the steps of: (a) culturing the host cell containing an expression vector containing at least a fragment of a polynucleotide sequence encoding HUPM under conditions suitable for the expression of the polypeptide; and (b) recovering the polypeptide from the host cell culture.

The invention also provides a pharmaceutical composition comprising a substantially purified HUPM having the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12, or fragments thereof, in conjunction with a suitable pharmaceutical carrier.

The invention further includes a purified antibody which binds to a polypeptide comprising the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12, or fragments thereof, as well as a purified agonist and a purified antagonist to the polypeptide.

The invention also provides a method for treating or preventing a cell proliferative disorder associated with increased expression or activity of HUPM, the method comprising administering to a subject in need of such treatment an effective amount of an antagonist of HUPM.

The invention also provides a method for treating or preventing an immune disorder associated with increased expression or activity of HUPM, the method comprising administering to a subject in need of such treatment an effective amount of an antagonist of HUPM.

The invention also provides a method for treating or preventing a cell proliferative disorder associated with decreased expression or activity of HUPM, the method comprising administering to a subject in need of such treatment an effective amount of a pharmaceutical composition comprising HUPM in conjunction with a suitable pharmaceutical carrier.

The invention also provides a method for treating or preventing an immune disorder associated with decreased expression or activity of HUPM, the method comprising administering to a subject in need of such treatment an effective amount of a pharmaceutical composition comprising HUPM in conjunction with a suitable pharmaceutical carrier.

The invention also provides a method for detecting a polynucleotide encoding HUPM in a biological sample containing nucleic acids, the method comprising the steps of: (a) hybridizing the complement of the polynucleotide sequence encoding the polypeptide comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12, or fragments thereof to at least one of the nucleic acids of the biological sample, thereby forming a hybridization complex; and (b) detecting the hybridization complex, wherein the presence of the hybridization complex correlates with the presence of a polynucleotide encoding HUPM in the biological sample. In one aspect, the nucleic acids of the biological sample are amplified by the polymerase chain reaction prior to the hybridizing step.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HUPM," as used herein, refers to the amino acid sequences of substantially purified HUPM obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HUPM, increases or prolongs the duration of the effect of HUPM. Agonists may include proteins, nucleic acids, carbohydrates, or any other molecules which bind to and modulate the effect of HUPM.

An "allele" or an "allelic sequence," as these terms are used herein, is an alternative form of the gene encoding HUPM. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HUPM, as described herein, include those sequences with deletions, insertions, or substitutions of different nucleotides, resulting in a polynucleotide the same HUPM or a polypeptide with at least one functional characteristic of HUPM. Included within this definition are polymorphisms which may or may not be readily detectable using a particular oligonucleotide probe of the polynucleotide encoding HUPM, and improper or unexpected hybridization to alleles, with a locus other than the normal chromosomal locus for the polynucleotide sequence encoding HUPM. The encoded protein may also be "altered," and may contain deletions, insertions, or substitutions of amino acid residues which produce a silent change and result in a functionally equivalent HUPM. Deliberate amino acid substitutions may be made on the basis of similarity in polarity, charge, solubility, hydrophobicity, hydrophilicity, and/or the amphipathic nature of the residues, as long as the biological or immunological activity of HUPM is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HUPM which are preferably about 5 to about 15 amino acids in length and which retain some biological activity or immunological activity of HUPM. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to HUPM, decreases the amount or the duration of the effect of the biological or immunological activity of HUPM. Antagonists may include proteins, nucleic acids, carbohydrates, antibodies, or any other molecules which decrease the effect of HUPM.

As used herein, the term "antibody" refers to intact molecules as well as to fragments thereof, such as Fa, F(ab')$_2$, and Fv fragments, which are capable of binding the epitopic determinant. Antibodies that bind HUPM polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HUPM, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition.

Compositions comprising polynucleotide sequences encoding HUPM or fragments of HUPM may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (PE Biosystems, Foster City, Calif.) in the 5' and/or the 3' direction, and resequenced, or which has been assembled from the overlapping sequences of more than one Incyte Clone using a computer program for fragment assembly, such as the GELVIEW Fragment Assembly system (Genetics Computer Group, Madison Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HUPM, by northern analysis is indicative of the presence of nucleic acids encoding HUPM in a sample, and thereby correlates with expression of the transcript from the polynucleotide encoding HUPM.

A "deletion," as the term is used herein, refers to a change in the amino acid or nucleotide sequence that results in the absence of one or more amino acid residues or nucleotides.

The term "derivative," as used herein, refers to the chemical modification of HUPM, of a polynucleotide sequence encoding HUPM, or of a polynucleotide sequence complementary to a polynucleotide sequence encoding HUPM. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains a at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison Wis.). This program can create alignments between two or more sequences according to different methods, e.g., the clustal method. (Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A. minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, such as the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides or oligonucleotides on a substrate, such as paper, nylon or any other type of membrane, filter, chip, glass slide, or any other suitable solid support.

The term "modulate," as it appears herein, refers to a change in the activity of HUPM. For example, modulation may cause an increase or a decrease in protein activity, binding characteristics, or any other biological, functional, or immunological properties of HUPM.

The phrases "nucleic acid" or "nucleic acid sequence," as used herein, refer to an oligonucleotide, nucleotide, polynucleotide, or any fragment thereof, to DNA or RNA of genomic or synthetic origin which maybe single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HUPM, or fragments thereof, or HUPM itself, may comprise a bodily fluid; an extract from a cell, chromosome, organelle, or membrane isolated from a cell; a cell; genomic DNA, RNA, or cDNA. in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and transiently transformed cells which express the inserted DNA or RNA for limited periods of time.

A "variant" of HUPM, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of new human protease molecules (HUPM), the polynucleotides encoding HUPM, and the use of these compositions for the diagnosis, treatment, or prevention of cell proliferative and immune disorders. Table 1 shows the sequence identification numbers, Incyte Clone identification number, and cDNA library for each of the human protease molecules disclosed herein.

TABLE 1

| PROTEIN | NUCLEOTIDE | CLONE ID | LIBRARY |
| --- | --- | --- | --- |
| SEQ ID NO:1 | SEQ ID NO:13 | 135360 | BMARNOT02 |
| SEQ ID NO:2 | SEQ ID NO:14 | 447484 | TLYMNOT02 |
| SEQ ID NO:3 | SEQ ID NO:15 | 789927 | PROSTUT03 |
| SEQ ID NO:4 | SEQ ID NO:16 | 877617 | LUNGAST01 |
| SEQ ID NO:5 | SEQ ID NO:17 | 999322 | KIDNTUT01 |
| SEQ ID NO:6 | SEQ ID NO:18 | 1337018 | COLNNOT13 |
| SEQ ID NO:7 | SEQ ID NO:19 | 1798496 | COLNNOT27 |
| SEQ ID NO:8 | SEQ ID NO:20 | 2082147 | UTRSNOT08 |
| SEQ ID NO:9 | SEQ ID NO:21 | 2170967 | ENDCNOT03 |
| SEQ ID NO:10 | SEQ ID NO:22 | 2484218 | SMCANOT01 |
| SEQ ID NO:11 | SEQ ID NO:23 | 2680548 | SINIUCT01 |
| SEQ ID NO:12 | SEQ ID NO:24 | 29579691 | KIDNFET01 |

Nucleic acids encoding the HUPM-1 of the present invention were first identified in Incyte Clone 135360 from the bone marrow cDNA library (BMARNOT02) using a computer search for amino acid sequence alignments. A consensus sequence, SEQ ID NO:13, was derived from the following overlapping and/or extended nucleic acid sequences: Incyte Clones 135360 (BMARNOT02), 1440654 (THYRNOT03), 1985677 (LUNGAST01), 2016316 (ENDCNOT03), 2309369 (NGANNOT01), 3003105 (TLYMNOT06), and 3604791 (LUNGNOT30).

In one embodiment, the invention encompasses a polypeptide comprising the amino acid sequence of SEQ ID NO:1. HUPM-1 is 63 amino acids in length and, has chemical and structural homology with rat proteasome subunit, C8 (GI 203207). In particular, HUPM-1 and rat C8 share 54% identity. The fragment of SEQ ID NO:13 from about nucleotide 688 to about nucleotide 744 is useful for hybridization. Northern analysis shows the expression of this sequence in cardiovascular, male and female reproductive, and gastrointestinal cDNA libraries. Approximately 25% of these libraries are associated with neoplastic disorders and 33% with inflammation and the immune response.

Nucleic acids encoding the HUPM-2 of the present invention were first identified in Incyte Clone 447484 from the T-lymphocyte cDNA library (TYLMNOT02) using a computer search for amino acid sequence alignments. A consensus sequence, SEQ ID NO:14, was derived from the following overlapping and/or extended nucleic acid sequences: Incyte Clones 007562 (HMC1NOT01), 288369 (EOSIHET02), 447484 (TLYMNOT02), 1357876 (LUNGNOT09), 1688150 (PROSTUT10), 2506075 (CONUTUT01), 2748364 (LUNGTUT11), and shotgun sequences SAJA02963, SAJA00487, and SAJA00384.

In another embodiment, the invention encompasses a polypeptide comprising the amino acid sequence of SEQ ID NO:2. HUPM-2 is 262 amino acids in length and has a potential N-glycosylation site at N91, and potential phosphorylation sites for casein kinase II at S55, S63, S97, and T168, and for protein kinase C at S97, S186, and T246. A potential catalytic active site triad for cysteine proteases is found in amino acid residues C36, D176, and H177. The fragment of SEQ ID NO:14 from about nucleotide 2242 to 2292 encompasses the active site cysteine encoding region of the molecule and is useful for hybridization. Northern analysis shows the expression of this sequence in cardiovascular, male and female reproductive, and hematopoietic cDNA libraries. Approximately 48% of these libraries are associated with neoplastic disorders and 24% with inflammation and the immune response.

Nucleic acids encoding the HUPM-3 of the present invention were first identified in Incyte Clone 789927 from the prostate tumor cDNA library (PROSTUT03) using a computer search for amino acid sequence alignments. A consensus sequence, SEQ ID NO:15, was derived from the following overlapping and/or extended nucleic acid sequences: Incyte Clones 789927 (PROSTUT03), 1646976 (PROSTUT09), and 1979791 (LUNGTUT03).

In another embodiment, the invention encompasses a polypeptide comprising the amino acid sequence of SEQ ID NO:3. HUPM-3 is 314 amino acids in length and has a potential signal peptide sequence between amino acid residues M1 and R19. Potential N-glycosylation sites are found at residues N167, N200, and N273, and potential phosphorylation sites are found for casein kinase II at T86, S134, S161, T190, and S291, and for protein kinase C at T39, S58, S73, S127, and S212. Sequences containing potential active site histidine and serine residues, characteristic of serine proteases, are found at LTAAH82 and GDS238GGP in HUPM-3. The fragment of SEQ ID NO:15 between about nucleotide 271 to about nucleotide 330 which encompasses the active site histidine is useful for hybridization. Northern analysis shows the expression of this sequence in cardiovascular, hematopoietic, and male reproductive cDNA libraries. Approximately 86% of these libraries are associated with neoplastic disorders.

Nucleic acids encoding the HUPM-4 of the present invention were first identified in Incyte Clone 877617 from the lung cDNA library (LUNGAST01) using a computer search for amino acid sequence alignments. A consensus sequence, SEQ ID NO:16, was derived from the following overlapping and/or extended nucleic acid sequences: Incyte Clones 372314 (LUNGNOT02), 698335 (SYNORAT03), 692718 (LUNGTUT02), 877617 (LUNGAST01), and 1399470 (BRAITUT08).

In another embodiment, the invention encompasses a polypeptide comprising the amino acid sequence of SEQ ID NO:4. HUPM-4 is 420 amino acids in length and has a potential signal peptide sequence extending from residues M1 to P21. Potential N-glycosylation sites are found at residues N90, N133, and N336. Potential phosphorylation sites are found for casein kinase II at S60 and T338, and for protein kinase C at S106, T143, T346, and S393. Two potential leucine zipper patterns are found beginning at L309 and L316, and a potential cell attachment site is found in the sequence R387GD. Two potential active site aspartate residues, characteristic of aspartic proteases, are found at residues D96 and D283. The fragment of SEQ ID NO:16 from about nucleotide 1609 to about nucleotide 1692, encompassing a leucine zipper domain, is useful for hybridization. Northern analysis shows the expression of this sequence in cardiovascular, hematopoietic, and male and female reproductive cDNA libraries. Approximately 56% of these libraries are associated with neoplastic disorders, 18% with inflammation and the immune response, and 18% with trauma.

Nucleic acids encoding the HUPM-5 of the present invention were first identified in Incyte Clone 999322 from the kidney tumor cDNA library (KIDNTUT01) using a computer search for amino acid sequence alignments, and a consensus sequence, SEQ ID NO:17, was derived from this clone.

In another embodiment, the invention encompasses a polypeptide comprising the amino acid sequence of SEQ ID NO:5. HUPM-5 is 200 amino acids in length and has a potential N-glycosylation site at N121, and potential phosphorylation sites for cAMP- and cGMP-dependent protein kinase at S35, for casein kinase II at S150 and T158, and for protein kinase C at T180. A potential active site serine for serine protease is found in the sequence GDS112GGP. The fragment of SEQ ID NO:17 from about nucleotide 775 to about nucleotide 838 from the active site serine domain is useful for hybridization. Northern analysis shows the expression of this sequence exclusively in kidney tumor (KIDNTUT01).

Nucleic acids encoding the HUPM-6 of the present invention were first identified in Incyte Clone 1337018 from the colon cDNA library (COLNNOT13) using a computer search for amino acid sequence alignments. A consensus sequence, SEQ ID NO:18, was derived from the following overlapping and/or extended nucleic acid sequences: Incyte Clones 1271725 (TESTTUT02),1337018 (COLNNOT13), 586982 and 588598 (UTRSNOT01).

In another embodiment, the invention encompasses a polypeptide comprising the amino acid sequence of SEQ ID NO:6. HUPM-6 is 435 amino acids in length and has potential N-glycosylation sites at residues N128 and N176, potential phosphorylation sites for cAMP- and cGMP-dependent protein kinase T249, for casein kinase II at S93 and S231, for protein kinase C at T26, S144, T148, S197, T200, S260, T303, S351, and T365, and for tyrosine kinase at Y59 and Y360. Sequences containing potential active site histidine and serine residues for serine proteases are found at LTAAH243C and GDS385GGP, respectively. The fragment of SEQ ID NO:18 from about nucleotide 900 to about nucleotide 949 encompassing the active site histidine residue is useful for hybridization. Northern analysis shows the expression of this sequence in gastrointestinal and male and female reproductive cDNA libraries. Approximately 65% of these libraries are associated with neoplastic disorders and 22% with the immune response.

Nucleic acids encoding the HUPM-7 of the present invention were first identified in Incyte Clone 1798496 from the colon cDNA library (COLNNOT27) using a computer search for amino acid sequence alignments. A consensus sequence, SEQ ID NO:19, was derived from the following overlapping and/or extended nucleic acid sequences: Incyte Clones 819896 (KERANOT02),1798496 (COLNNOT27), and shotgun sequence SAGA00119.

In another embodiment, the invention encompasses a polypeptide comprising the amino acid sequence of SEQ ID NO:7. HUPM-7 is 260 amino acids in length and has a potential signal peptide sequence extending from residues M1 to A28. Potential N-myristolyation sites are found in the vicinity of the signal peptide cleavage site at G19, G20, and G35. A potential N-glycosylation site is found at N110, and potential phosphorylation sites are found for casein kinase II at S112,S140, and S162, for protein kinase C at T80, S162, S201, and S236, and for tyrosine kinase at Y188. A potential glycosaminoglycan attachment site is found at S155, and sequences containing potential active site histidine and serine residues for serine proteases are found at LTAAH73C and GDS212GGP, respectively. The fragment of SEQ ID NO:19 from about nucleotide 517 to about nucleotide 574, located between the active site histidine and serine residues, is useful for hybridization. Northern analysis shows the expression of this sequence in female reproductive, neural, lung, and colon cDNA libraries. Approximately 83% of these libraries are associated with neoplastic disorders.

Nucleic acids encoding the HUPM-8 of the present invention were first identified in Incyte Clone 2082147 from the uterine tissue cDNA library (UTRSNOT08) using a computer search for amino acid sequence alignments. A consensus sequence, SEQ ID NO:20, was derived from the following overlapping and/or extended nucleic acid sequences: Incyte Clones 586776 (UTRSNOT01), 1719194 (BLADNOT06), 2082147 and 2082170 (UTRSNOT08), 3359814 (PROSTUT16), and shotgun sequences SAGA01368 and SAGA01895.

In another embodiment, the invention encompasses a polypeptide comprising the amino acid sequence of SEQ ID NO:8. HUPM-8 is 175 amino acids in length and has a potential signal peptide sequence extending between residues M1 and L30, potential phosphorylation sites for casein kinase II at T28, and for protein kinase C at S81. A potential cell attachment site sequence is found at R73DG, and a potential signal peptidase signature sequence containing an active site serine residue is found in the sequence GDHHGHS128FD. The fragment of SEQ ID NO:20 from about nucleotide 757 to about nucleotide 789 from the catalytic active site is useful for hybridization. Northern analysis shows the expression of this sequence in fetal, gastrointestinal, male and female reproductive, and neuronal cDNA libraries. Approximately 38% of these libraries are associated with neoplastic disorders, 24% with the immune response, and 14% with fetal development.

Nucleic acids encoding the HUPM-9 of the present invention were first identified in Incyte Clone 2170967 from the endothelial cell cDNA library (ENDCNOT03) using a computer search for amino acid sequence alignments. A consensus sequence, SEQ ID NO:21, was derived from the following overlapping and/or extended nucleic acid sequences: Incyte Clones 1667462 (BMARNOT03), 1830465 (THP1AZT01), 1888989 (BLADTUT07), 1928627 (BRSTNOT02), 2170967 (ENDCNOT03), 3125590 (LUNGTUT12), and 3456567 (293TF1T01).

In another embodiment, the invention encompasses a polypeptide comprising the amino acid sequence of SEQ ID NO:9. HUPM-9 is 519 amino acids in length and has a potential aminopeptidase signature sequence at N362TDAEGRL in which D364 and E366 represent the zinc binding ligands at the active site. HUPM-9 also has two potential N-glycosylation sites at N72 and N410, and potential phosphorylation sites for casein kinase II at S28, S54, S138, S228, S238, T363, T487, and T506, and for protein kinase C at S174, S227, S292, S340, T487, and T500. The fragment of SEQ ID NO:21 from about nucleotide 688 to about nucleotide 747 is useful for hybridization. Northern analysis shows the expression of this sequence in cardiovascular, male and female reproductive, hematopoietic, and nervous system cDNA libraries. Approximately 46% of these libraries are associated with neoplastic disorders and 31% with the immune response.

Nucleic acids encoding the HUPM-10 of the present invention were first identified in Incyte Clone 2484218 from the aortic smooth muscle cell cDNA library (SMCANOT01) using a computer search for amino acid sequence alignments. A consensus sequence, SEQ ID NO:22, was derived from the following overlapping and/or extended nucleic acid sequences: Incyte Clones 1351043 (LATRTUT02), 1381980 (BRAITUT08), 1432027 (BEPINON01), 1457881 (COLNFET02), and 2484218 (SMCANOT01).

In another embodiment, the invention encompasses a polypeptide comprising the amino acid sequence of SEQ ID NO:10. HUPM-10 is 327 amino acids in length and has three potential N-glycosylation sites at N12, N50, and N214, and potential phosphorylation sites for casein kinase II at S18, T93, T107, S166, S170, and T216, for protein kinase C at T272, and for tyrosine kinase at Y104. HUPM-10 has chemical and structural homology with human proteasome subunit p40 (GI971270). In particular, HUPM-10 and human p40 share 23% homology. The fragment of SEQ ID NO:22 from about nucleotide 136 to about nucleotide 211 is useful for hybridization. Northern analysis shows the expression of this sequence in cardiovascular, male and female reproductive, nervous system, and hematopoietic cDNA libraries. Approximately 40% of these libraries are associated with neoplastic disorders, 24% with the immune response, and 22% with fetal development.

Nucleic acids encoding the HUPM-11 of the present invention were first identified in Incyte Clone 2680548 from the ileum tissue cDNA library (SINIUCT01) using a computer search for amino acid sequence alignments. A consensus sequence, SEQ ID NO:23, was derived from the following overlapping and/or extended nucleic acid sequences: Incyte Clones 725100 (SYNOOAT01), 779975 (MYOMNOT01), 1528274(UCMCL5T01), 1658964 (URETTUT01), 1781933 (PGANNON02), 2618786 (GBLANOT01), and 2680548 (SINIUCT01).

In another embodiment, the invention encompasses a polypeptide comprising the amino acid sequence of SEQ ID NO:11. HUPM-11 is 458 amino acids in length and has two sequences containing potential active site histidine and serine residues for serine proteases at VTNAH198V and GNS306GGP, respectively. Two potential N-glycosylation sites are found at N181 and N349, and potential phosphorylation sites are found for cAMP- and cGMP-dependent protein kinase at S350, for casein kinase II at T221, T290, and S383, and for protein kinase C at S13, S142, T231, T322, S335, and S337. The fragment of SEQ ID NO:23 from about nucleotide 694 to about nucleotide 756, located between the potential histidine and serine active site residues, is useful for hybridization. Northern analysis shows the expression of this sequence in gastrointestinal, male and female reproductive, and nervous system cDNA libraries. Approximately 43% of these libraries are associated with neoplastic disorders and 25% with the immune response.

Nucleic acids encoding the HUPM-12 of the present invention were first identified in Incyte Clone 2957969 from the fetal kidney cDNA library (KIDNFET01) using a computer search for amino acid sequence alignments. A consensus sequence, SEQ ID NO:24, was derived from the following overlapping and/or extended nucleic acid sequences: Incyte Clones 875973 (LUNGAST01), 978220 (BRSTNOT02), 1362955 (LUNGNOT12), 1511581 (LUNGNOT14), 2354566 (LUNGNOT20), 2957969 (KIDNFET01), and 3676880 (PLACNOT07).

In another embodiment, the invention encompasses a polypeptide comprising the amino acid sequence of SEQ ID NO:12. HUPM-12 is 532 amino acids in length and has three potential N-glycosylation sites at N182, N329, and N348, potential phosphorylation sites for casein kinase II at S20, T205, T331, T350, and S441, and for protein kinase C at T144, S150, S279, S341, T388, and S526. A potential aminopeptidase signature sequence is found at N349TDAEGRL in which D351 and E353 represent the zinc binding ligands at the active site. A potential ATP/GTP-binding site (P-loop) is also found in the sequence G277LSIKGKT. The fragment of SEQ ID NO:24 from about nucleotide 709 to about nucleotide 781 is useful for hybridization. Northern analysis shows the expression of this sequence in cardiovascular, male and female reproductive, and nervous system cDNA libraries. Approximately 55% of these libraries are associated with neoplastic disorders, 12% with the immune response, and 14% with fetal tissues and proliferative cell lines.

The invention also encompasses HUPM variants. A preferred HUPM variant is one which has at least about 80%, more preferably at least about 90%, and most preferably at least about 95% amino acid sequence identity to the HUPM amino acid sequence, and which contains at least one functional or structural characteristic of HUPM.

The invention also encompasses polynucleotides which encode HUPM. In a particular embodiment, the invention encompasses a polynucleotide consisting of a nucleic acid sequence selected from the group consisting of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24.

The invention also encompasses a variant of a polynucleotide sequence encoding HUPM. In particular, such a variant polynucleotide sequence will have at least about 80%, more preferably at least about 90%, and most preferably at least about 95% polynucleotide sequence identity to the polynucleotide sequence encoding HUPM. A particular aspect of the invention encompasses a variant of a polynucleotide sequence selected from the group consisting of SEQ ID NO:13 SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24 which has at least about 80%, more preferably at least about 90%, and most preferably at least about 95% polynucleotide sequence identity to a polynucleotide sequence selected from the group consisting of SEQ ID NO:13 SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24. Any one of the polynucleotide variants described above can encode an amino acid sequence which contains at least one functional or structural characteristic of HUPM.

It will be appreciated by those skilled in the art that as a result of the degeneracy of the genetic code, a multitude of polynucleotide sequences encoding HUPM, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HUPM, and all such variations are to be considered as being specifically disclosed.

Although nucleotide sequences which encode HUPM and its variants are preferably capable of hybridizing to the nucleotide sequence of the naturally occurring HUPM under appropriately selected conditions of stringency, it may be advantageous to produce nucleotide sequences encoding HUPM or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HUPM and its derivatives without altering the encoded amino acid sequences include the production of RNA transcripts having more desirable properties, such as a greater half-life, than transcripts produced from the naturally occurring sequence.

The invention also encompasses production of DNA sequences which encode HUPM and HUPM derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HUPM or any fragment thereof.

Also encompassed by the invention are polynucleotide sequences that are capable of hybridizing to the claimed polynucleotide sequences, and, in particular, to those shown in SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24, or fragments thereof under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Rockville Md.). Preferably, sequence preparation is automated with machines such as the HYDRA microdispenser (Robbins Scientific, Sunnyvale Calif.), MICROLAB 2200 (Hamilton, Reno Nev.), and the DNA ENGINE thermal cycler (PTC200; MJ Research, Watertown Mass.). Machines used for sequencing include the ABI 3700, 377 or 373 DNA sequencing systems (PE Biosystems), the MEGABACE 1000 DNA sequencing system (APB), and the like. The sequences maybe analyzed using a variety of algorithms which are well known in the art and described in Ausubel (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

The nucleic acid sequences encoding HUPM may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences, Plymouth Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR, PE Biosystems), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HUPM may be used in recombinant DNA molecules to direct expression of HUPM, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HUPM.

As will be understood by those of skill in the art, it may be advantageous to produce HUPM-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HUPM-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HUPM may be ligated to a heterologous sequence to encode a fusion protein. For example, to screen peptide libraries for inhibitors of HUPM activity, it may be useful to encode a chimeric HUPM protein that can be recognized by a commercially available antibody. A fusion protein may also be engineered to contain a cleavage site located between the HUPM encoding sequence and the heterologous protein sequence, so that HUPM may be cleaved and purified away from the heterologous moiety.

In another embodiment, sequences encoding HUPM may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, the protein itself may be produced using chemical methods to synthesize the amino acid sequence of HUPM, or a fragment thereof. For example, peptide synthesis can be performed using various solid-phase techniques. (See, e.g. Roberge, J. Y. et al. (1995) Science 269:202–204.) Automated synthesis may be achieved using the ABI 431A peptide synthesizer (PE Biosystems). Additionally, the amino acid sequence of HUPM, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular Properties*, WH Freeman and Co., New York, N.Y.)

In order to express a biologically active HUPM, the nucleotide sequences encoding HUPM or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HUPM and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HUPM. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems.

The invention is not limited by the host cell employed.

The "control elements" or "regulatory sequences" are those non-translated regions, e.g., enhancers, promoters, and 5' and 3' untranslated regions, of the vector and polynucleotide sequences encoding HUPM which interact with host cellular proteins to carry out transcription and translation. Such elements may vary in their strength and specificity.

Depending on the vector system and host utilized, any number of suitable transcription and translation elements, including constitutive and inducible promoters, may be used. For example, when cloning in bacterial systems, inducible promoters, e.g., hybrid lacZ promoter of the PBLUESCRIPT vector (Stratagene, La Jolla Calif.) or PSPORT1 plasmid (Life Technologies), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HUPM, vectors based on SV40 or EBV may be used with an appropriate selectable marker.

In bacterial systems, a number of expression vectors may be selected depending upon the use intended for HUPM. For example, when large quantities of HUPM are needed for the induction of antibodies, vectors which direct high level expression of fusion proteins that are readily purified may be used. Such vectors include, but are not limited to, multifunctional *E. coli* cloning and expression vectors such as PBLUESCRIPT (Stratagene), in which the sequence encoding HUPM may be ligated into the vector in frame with sequences for the amino-terminal Met and the subsequent 7 residues of β-galactosidase so that a hybrid protein is produced, and PSPORT vectors (Life Technologies) pGEX vectors (Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcoholoxidase, and PGH, maybe used. (See, e.g., Ausubel, supra; and Grant et al. (1987) Methods Enzymol. 153:516–544.)

In cases where plant expression vectors are used, the expression of sequences encoding HUPM may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HUPM. For example, in one such system, *Autographa californica* nuclear polyhedrosis virus (AcNPV) is used as a vector to express foreign genes in *Spodoptera frugiperda* cells or in *Trichoplusia* larvae. The sequences encoding HUPM maybe cloned into a non-essential region of the virus, such as the polyhedrin gene, and placed under control of the polyhedrinpromoter. Successful insertion of sequences encoding HUPM will render the polyhedrin gene inactive and produce recombinant virus lacking coat protein. The recombinant viruses may then be used to infect, for example, *S. frugiperda* cells or *Trichoplusia* larvae in which HUPM may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HUPM maybe ligated into an adenovirus transcription/translation complex consisting of the late promoter and tripartite leader sequence. Insertion in a non-essential E1 or E3 region of the viral genome may be used to obtain a viable virus which is capable of expressing HUPM in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HUPM. Such signals include the ATG initiation codon and adjacent sequences. In cases where sequences encoding HUPM and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HUPM can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in $tk^-$ or $apr^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Recently, the use of visible markers, such as anthocyanins, green fluorescent proteins, β glucuronidase and its substrate GUS, luciferase and its substrate luciferin, has increased. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HUPM is inserted within a marker gene sequence, transformed cells containing sequences encoding HUPM can be identified by the absence of marker gene function. Alternatively, a marker gene can be placed in tandem with a sequence encoding HUPM under the control of a single promoter. Expression of the marker gene in response to induction or selection usually indicates expression of the tandem gene as well.

Alternatively, host cells which contain the nucleic acid sequence encoding HUPM and express HUPM may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HUPM can be detected by DNA-DNA or DNA-RNA hybridization or amplification using probes or fragments or fragments of polynucleotides encoding HUPM. Nucleic acid amplification based assays involve the use of oligonucleotides or oligomers based on the sequences encoding HUPM to detect transformants containing DNA or RNA encoding HUPM.

A variety of protocols for detecting and measuring the expression of HUPM, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HUPM is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HUPM include oligolabeling, nick translation, end-labeling, or PCR amplification using a labeled nucleotide. Alternatively, the sequences encoding HUPM, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HUPM may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HUPM may be designed to contain signal sequences which direct secretion of HUPM through a prokaryotic or eukaryotic cell membrane. Other constructions may be used to join sequences encoding HUPM to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HUPM encoding sequence may be used to facilitate purification. One such expression vector provides for expression of a fusion protein containing HUPM and a nucleic acid encoding 6 histidine residues preceding a thioredoxin or an enterokinase cleavage site. The histidine residues facilitate purification on immobilized metal ion affinity chromatography (IMIAC). (See, e.g., Porath, J. et al. (1992) Prot. Exp. Purif. 3: 263–281.) The enterokinase cleavage site provides a means for purifying HUPM from the fusion protein. (See, e.g., Kroll, D. J. et al. (1993) DNA Cell Biol. 12:441–453.)

Fragments of HUPM may be produced not only by recombinant production, but also by direct peptide synthesis using solid-phase techniques. (See, e.g., Creighton, T. E. (1984) Protein: Structures and Molecular Properties, pp. 55–60, W.H. Freeman and Co., New York, N.Y.) Protein synthesis may be performed by manual techniques or by automation. Automated synthesis may be achieved, for example, using the Applied Biosystems 431 A Peptide Synthesizer (Perkin Elmer). Various fragments of HUPM may be synthesized separately and then combined to produce the full length molecule.

Therapeutics

Chemical and structural homology exists among the human protease molecules of the invention. In addition, HUPM is expressed in proliferating cell types associated with cancer, and the immune response. Therefore, HUPM appears to play a role in cell proliferative disorders and immune disorders. Therefore, in cell proliferative or immune disorders where HUPM is being expressed or is promoting cell proliferation it is desirable to decrease the expression of HUPM. In cell proliferative or immune disorders where expression of HUPM is decreased, it is desirable to provide the protein or increase expression.

Therefore, in one embodiment, an antagonist of HUPM may be administered to a subject to treat or prevent a cell proliferative disorder associated with increased expression or activity of HUPM. Such a disorder may include, but is not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gallbladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HUPM may be used directly as an antagonist or indirectly as a targeting or delivery mechanism for bringing a pharmaceutical agent to cells or tissue which express HUPM.

In another additional embodiment, a vector expressing the complement of the polynucleotide encoding HUPM may be administered to a subject to treat or prevent a cell proliferative disorder including, but not limited to, those described above.

In another embodiment, an antagonist of HUPM may be administered to a subject to treat or prevent an immune disorder associated with increased expression or activity of HUPM. Such a disorder may include, but is not limited to AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In still another embodiment, a vector expressing the complement of the polynucleotide encoding HUPM may be administered to a subject to treat or prevent an immune disorder including, but not limited to, those described above.

In another embodiment, HUPM or a fragment or derivative thereof may be administered to a subject to treat or prevent a cell proliferative disorder associated with decreased expression or activity of HUPM. Such disorders can include, but are not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HUPM or a fragment or derivative thereof may be administered to a subject to treat or prevent a cell proliferative disorder including, but not limited to, those described above.

In a further embodiment, a pharmaceutical composition comprising a substantially purified HUPM in conjunction with a suitable pharmaceutical carrier may be administered to a subject to treat or prevent a cell proliferative disorder including, but not limited to, those provided above.

In still another embodiment, an agonist which modulates the activity of HUPM may be administered to a subject to treat or prevent a cell proliferative disorder including, but not limited to, those listed above.

In another embodiment, HUPM or a fragment or derivative thereof may be administered to a subject to treat or prevent an immune disorder associated with decreased expression or activity of HUPM. Such disorders can include, but are not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, lungal, parasitic, protozoal, and helminthic infections; and trauma.

In another embodiment, a vector capable of expressing HUPM or a fragment or derivative thereof may be administered to a subject to treat or prevent an immune disorder including, but not limited to, those described above.

In a further embodiment, a pharmaceutical composition comprising a substantially purified HUPM in conjunction with a suitable pharmaceutical carrier may be administered to a subject to treat or prevent an immune disorder including, but not limited to, those provided above.

In still another embodiment, an agonist which modulates the activity of HUPM may be administered to a subject to treat or prevent an immune disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HUPM may be produced using methods which are generally known in the art. In particular, purified HUPM may be used to produce antibodies or to screen libraries of pharmaceutical agents to identify those which specifically bind HUPM. Antibodies to HUPM may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HUPM or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HUPM have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HUPM amino acids may be fused with those of another protein, such as KLH, and antibodies to the chimeric molecule may be produced.

Monoclonal antibodies to HUPM may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42;Cote, R. J. etal. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HUPM-specific single chain antibodies. Antibodies with related specificity, but of distinct idiotypic composition, maybe generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HUPM may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HUPM and its specific antibody. A two-site, monoclonal-based immunoassay utilizing monoclonal antibodies reactive to two non-interfering HUPM epitopes is preferred, but a competitive binding assay may also be employed. (Maddox, supra.)

In another embodiment of the invention, the polynucleotides encoding HUPM, or any fragment or complement thereof, may be used for therapeutic purposes. In one aspect, the complement of the polynucleotide encoding HUPM may be used in situations in which it would be desirable to block the transcription of the mRNA. In particular, cells may be transformed with sequences complementary to polynucleotides encoding HUPM. Thus, complementary molecules or fragments may be used to modulate HUPM activity, or to achieve regulation of gene function. Such technology is now well known in the art, and sense or antisense oligonucleotides or larger fragments can be designed from various locations along the coding or control regions of sequences encoding HUPM.

Expression vectors derived from retroviruses, adenoviruses, or herpes or vaccinia viruses, or from various bacterial plasmids, maybe used for delivery of nucleotide sequences to the targeted organ, tissue, or cell population. Methods which are well known to those skilled in the art can be used to construct vectors which will express nucleic acid sequences complementary to the polynucleotides of the gene encoding HUPM. (See, e.g., Sambrook, supra; and Ausubel, supra.)

Genes encoding HUPM can be turned off by transforming a cell or tissue with expression vectors which express high levels of a polynucleotide, or fragment thereof, encoding HUPM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HUPM. Oligonucleotides derived from the transcription initiation site, e.g., between about positions –10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HUPM.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention maybe prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HUPM. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HUPM, antibodies to HUPM, and mimetics, agonists, antagonists, or inhibitors of HUPM. The compositions maybe administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HUPM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HUPM or fragments thereof, antibodies of HUPM, and agonists, antagonists or inhibitors of HUPM, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, and it can be expressed as the LD50/ED50 ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HUPM may be used for the diagnosis of disorders characterized by expression of HUPM, or in assays to monitor patients being treated with HUPM or agonists, antagonists, or inhibitors of HUPM. Antibodies useful for diagnostic purposes may be prepared in the same manner as described above for therapeutics. Diagnostic assays for HUPM include methods which utilize the antibody and a label to detect HUPM in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HUPM, including ELISAs, RIAs, and FACS, are known in the art and provide a basis for diagnosing altered or abnormal levels of HUPM expression. Normal or standard values for HUPM expression are established by combining body fluids or cell extracts taken from normal mammalian subjects, preferably human, with antibody to HUPM under conditions suitable for complex formation. The amount of standard complex formation may be quantitated by various methods, preferably by photometric means. Quantities of HUPM expressed in subject samples, control, and disease, from biopsied tissues are compared with the standard values. Deviation between standard and subject values establishes the parameters for diagnosing disease.

In another embodiment of the invention, the polynucleotides encoding HUPM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HUPM may be correlated with disease. The diagnostic assay may be used to determine absence, presence, and excess expression of HUPM, and to monitor regulation of HUPM levels during therapeutic intervention.

In one aspect, hybridization with PCR probes which are capable of detecting polynucleotide sequences, including genomic sequences, encoding HUPM or closely related molecules may be used to identify nucleic acid sequences which encode HUPM. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HUPM, alleles, or related sequences.

Probes may also be used for the detection of related sequences, and should preferably contain at least 50% identity to the nucleotides from any of the HUPM encoding sequences. The hybridization probes of the subject invention may be DNA or RNA and may be derived from the sequence of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24 or from genonuc sequences including promoters, enhancers, and introns of the HUPM gene.

Means for producing specific hybridization probes for DNAs encoding HUPM include the cloning of polynucleotide sequences encoding HUPM or HUPM derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding HUPM may be used for the diagnosis of a disorder associated with expression of HUPM. Examples of such a disorder include, but are not limited to, cell proliferative disorders such as arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding HUPM may be used in Southern or northern analysis, dot blot, or other membrane-based technologies; in PCR technologies; in dipstick, pin, and ELISA assays; and in microarrays utilizing fluids or tissues from patients to detect altered HUPM expression. Such qualitative or quantitative methods are well known in the art.

In a particular aspect, the nucleotide sequences encoding HUPM may be useful in assays that detect the presence of associated disorders, particularly those mentioned above. The nucleotide sequences encoding HUPM may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HUPM in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HUPM, a normal or standard profile for expression is established. This may be accomplished by combining body fluids or cell extracts taken from normal subjects, either animal or human, with a sequence, or a fragment thereof, encoding HUPM, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HUPM may involve the use of PCR. These oligomers may be chemically synthesized, generated enzymatically, or produced in vitro. Oligomers will preferably contain a fragment of a polynucleotide encoding HUPM, or a fragment of a polynucleotide complementary to the polynucleotide encoding HUPM, and will be employed under optimized conditions for identification of a specific gene or condition. Oligomers may also be employed under less stringent conditions for detection or quantitation of closely related DNA or RNA sequences.

Methods which may also be used to quantitate the expression of HUPM include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

In one embodiment, the microarray is prepared and used according to methods known in the art. (See, e.g., Chee et al. (1995) PCT application WO95/11995; Lockhart, D. J. et al. (1996) Nat. Biotech. 14:1675–1680; and Schena, M. et al. (1996) Proc. Natl. Acad. Sci. 93:10614–10619.)

The microarray is preferably composed of a large number of unique single-stranded nucleic acid sequences, usually either synthetic antisense oligonucleotides or fragments of cDNAs. The oligonucleotides are preferably about 6 to 60 nucleotides in length, more preferably about 15 to 30 nucleotides in length, and most preferably about 20 to 25 nucleotides in length. It may be preferable to use oligonucleotides which are about 7 to 10 nucleotides in length. The microarray may contain oligonucleotides which cover the known 5' or 3' sequence, sequential oligonucleotides which cover the full length sequence, or unique oligonucleotides selected from particular areas along the length of the sequence. Polynucleotides used in the microarray may be oligonucleotides specific to a gene or genes of interest. Oligonucleotides can also be specific to one or more unidentified cDNAs associated with a particular cell type or tissue type. It may be appropriate to use pairs of oligonucleotides on a microarray. The first oligonucleotide in each pair differs from the second oligonucleotide by one nucleotide. This nucleotide is preferably located in the center of the sequence. The second oligonucleotide serves as a control. The number of oligonucleotide pairs may range from about 2 to 1,000,000.

In order to produce oligonucleotides for use on a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack secondary structure that may interfere with hybridization. In one aspect, the oligomers may be synthesized on a substrate using a light-directed chemical process. (See, e.g., Chee et al., supra.) The substrate may be any suitable solid support, e.g., paper, nylon, any other type of membrane, or a filter, chip, or glass slide.

In another aspect, the oligonucleotides may be synthesized on the surface of the substrate using a chemical coupling procedure and an ink jet application apparatus. (See, e.g., Baldeschweiler et al. (1995) PCT application WO95/251116.) An array analogous to a dot or slot blot (HYBRIDOT apparatus, life Technologies) may be used to arrange and link cDNA fragments or oligonucleotides to the surface of a substrate using a vacuum system or thermal, UV, mechanical, or chemical bonding procedures. An array may also be produced by hand or by using available devices, materials, and machines, e.g. BRINKMANN multichannel pipettors or robotic instruments. The array may contain from 2 to 1,000,000 or any other feasible number of oligonucleotides.

In order to conduct sample analysis using the microarrays, polynucleotides are extracted from a sample. The sample may be obtained from any bodily fluid, e.g., blood, urine, saliva, phlegm, gastric juices, cultured cells, biopsies, or other tissue preparations. To produce probes, the polynucleotides extracted from the sample are used to produce nucleic acid sequences complementary to the nucleic acids on the microarray. If the microarray contains cDNAs, antisense RNAs (aRNAs) are appropriate probes. Therefore, in one aspect, mRNA is reverse-transcribed to cDNA. The cDNA, in the presence of fluorescent label, is used to produce fragment or oligonucleotide aRNA probes. The fluorescently labeled probes are incubated with the microarray so that the probes hybridize to the microarray oligonucleotides. Nucleic acid sequences used as probes can include polynucleotides, fragments, and complementary or antisense sequences produced using restriction enzymes, PCR, or other methods known in the art.

Hybridization conditions can be adjusted so that hybridization occurs with varying degrees of complementarity. A scanner can be used to determine the levels and patterns of fluorescence after removal of any nonhybridized probes. The degree of complementarity and the relative abundance of each oligonucleotide sequence on the microarray can be assessed through analysis of the scanned images. A detection system may be used to measure the absence, presence, or level of hybridization for any of the sequences. (See, e.g., Heller, R. A. et al. (1997) Proc. Natl. Acad. Sci. 94:2150–2155.)

In another embodiment of the invention, nucleic acid sequences encoding HUPM may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology,* VCH Publishers New York, N.Y., pp.965–968.) Examples of genetic map data can be found in various scientific journals or at the Online Mendelian Inheritance in Man (OMIM) site. Correlation between the location of the gene encoding HUPM on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HUPM, its catalytic or immunogenic fragments, or oligopeptides thereof can be used for screening libraries of compounds in any of a variety of drug screening techniques. The fragment employed in such screening maybe free in solution, affixed to a solid support, borne on a cell surface, or located intracellularly. The formation of binding complexes between HUPM and the agent being tested may be measured.

Another technique for drug screening provides for high throughput screening of compounds having suitable binding affinity to the protein of interest. (See, e.g., Geysen, et al. (1984) PCT application WO084/03564.) In this method, large numbers of different small test compounds are synthesized on a solid substrate, such as plastic pins or some other surface. The test compounds are reacted with HUPM, or fragments thereof, and washed. Bound HUPM is then detected by methods well known in the art. Purified HUPM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HUPM specifically compete with a test compound for binding HUPM. In this manner, antibodies can be used to detect the presence of any peptide which shares one or more antigenic determinants with HUPM.

In additional embodiments, the nucleotide sequences which encode HUPM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

For purposes of example, the preparation and sequencing of the PROSTUT03 cDNA library, from which Incyte Clone 789927 was isolated, is described. Preparation and sequencing of cDNAs in libraries in the LIFESEQ GOLD database (Incyte Genomics) have varied over time, and the gradual changes involved use of kits, plasmids, and machinery available at the particular time the library was made and analyzed.

I. PROSTUT03 cDNA Library Construction

The PROSTUT03 cDNA library was constructed from prostate tumor tissue removed from a 76-year-old Caucasian male by radical prostatectomy. The pathology report indicated a grade 3 (of 4) adenocarcinoma (Gleason grade 3+3) in the periphery of the prostate. Perineural invasion was present as was involvement of periprostatic tissue. Nontumorous portions of the prostate exhibited adenofibromatous hyperplasia. The patient had elevated levels of prostate specific antigen (PSA). Pelvic lymph nodes were negative for tumor. A prior stomach ulcer and atherosclerosis were reported in the patient history.

The frozen tissue was homogenized and lysedin in guanidinium isothiocyanate solution using a POLYTRON homogenizer (PT-3000; Brinkmann Instruments Westbury N.Y.). The lysate was extracted once with acid phenol at pH 4.0 per Stratagene's RNA isolation protocol (Stratagene) and once with phenol chloroform at pH 4.0. The RNA was precipitated using 0.3 M sodium acetate and 2.5 volumes of ethanol, resuspended in RNAse-free water, and treated with DNase at 37° C. RNA extraction and precipitation were repeated as before. The mRNA was isolated with the OLIGOTEX kit (Qiagen, Valencia Calif.) and used to construct the cDNA library.

The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors, and digested with NotI (New England Biolabs, Beverly Mass.). The cDNAs were fractionated on a SEPHAROSE CL-2B column (APB), and those cDNAs exceeding 800 bp were ligated into the NotI and EcoRI sites of the PSPORT1 plasmid (Life Technologies). The plasmid was transformed into competent DH5α cells (Life Technologies) or ELECTROMAX DH10B cells (Life Technologies).

II. Isolation and Sequencing of cDNA Clones

Plasmid DNA was released from the cells and purified using the MINIPREP kit (Edge Biosystems, Gaithersburg Md.). This kitconsists of a 96-well block with reagents for 960 purifications. The recommended protocol was employed except for the following changes: 1) the bacteria were cultured in 1 ml of sterile TERRIFIC BROTH (BD Biosciences) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4 C.

The cDNAs were prepared for sequencing using the MICROLAB 2200 system (Hamilton,) in combination with the DNA ENGINE thermal cyclers (MJ Research). The cDNAs were sequenced by the method of Sanger and Coulson (1975; J Mol Biol 94:441–448) using an ABI PRISM 377 sequencing system (PE Biosystems)

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool. (Altschul, S. F. (1993) J. Mol. Evol 36:290–300; and Altschul, et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides, and no more than 12% uncalled bases (where N can be A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or LIFESEQ database (Incyte Genomics). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HUPM occurs. Abundance and percent abundance are also reported. Abundance directly reflects the number of times a particular transcript is represented in a cDNA library, and percent abundance is abundance divided by the total number of sequences examined in the cDNA library.

V. Extension of HUPM Encoding Polynucleotides

The sequence of one of the polynucleotides of the present invention was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (PE Biosystems) and thoroughly mixing the enzyme and reaction mix. PCR was performed using the DNA ENGINE thermal cycler (MJ Research), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 1 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using a QIAQUICK column (Qiagen, Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2×Carb. The following day, several colonies were randomly picked from each plate and cultured in 150 µl of liquid LB/2×Carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

The nucleotide sequences of SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21. SEQ ID NO:22, SEQ ID NO:23, and SEQ ID NO:24 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 µCi of [γ-$^{32}$P] adenosine triphosphate (Amersham Pharmacia Biotech), and T4 polynucleotide kinase (DuPont NEN, Boston, Mass.). The labeled oligonucleotides are substantially purified using a SEPHADEX G-25 superfine resin column (Amersham Pharmacia Biotech). An aliquot containing 10⁷ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. Hybridization patterns are visualized using autoradiography or an alternative imaging means and compared.

VII. Microarrays

To produce oligonucleotides for a microarray, one of the nucleotide sequences of the present invention is examined using a computer algorithm which starts at the 3' end of the nucleotide sequence. For each, the algorithm identifies oligomers of defined length that are unique to the nucleic acid sequence, have a GC content within a range suitable for hybridization, and lack secondary structure that would interfere with hybridization. The algorithm identifies approximately 20 oligonucleotides corresponding to each nucleic acid sequence. For each sequence-specific oligonucleotide, a pair of oligonucleotides is synthesized in which the first oligonucleotides differs from the second oligonucleotide by one nucleotide in the center of the sequence. The oligonucleotide pairs can be arranged on a substrate, e.g. a silicon chip, using a light-directed chemical process. (See, e.g., Chee, supra.)

In the alternative, a chemical coupling procedure and an inkjet device can be used to synthesize oligomers on the surface of a substrate. (See, e.g., Baldeschweiler, supra.) An arrayanalogous to adot or slot blot may also be used to arrange and link fragments or oligonucleotides to the surface of a substrate using or thermal, UV, mechanical, or chemical bonding procedures, or a vacuum system. A typical array may be produced by hand or using available metods and machines and contain any appropriate number of elements. After hybridization, nonhybridized probes are removed and a scanner used to determine the levels and patterns of fluorescence. The degree of complementarity and the relative abundance of each oligonucleotide sequence on the microarray may be assessed through analysis of the scanned images.

VIII. Complementary Polynucleotides

Sequences complementary to the HUPM-encoding sequences, or any parts thereof, are used to detect, decrease, or inhibit expression of naturally occurring HUPM. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HUPM. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HUPM-encoding transcript.

IX. Expression of HUPM

Expression of HUPM is accomplished by subcloning the cDNA into an appropriate vector and transforming the vector into host cells. This vector contains an appropriate promoter, e.g., β-galactosidase upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HUPM into bacterial growth media which can be used directly in the following assay for activity.

X. Demonstration of HUPM Activity

Serine protease activity of HUPM is measured by the hydrolysis of various peptide thiobenzyl ester substrates. The substrates are chosen to represent the different SP types (chymase, trypase, aspase, etc.). Assays are performed at room temperature (~25° C.) and contain an aliquot of HUPM and the appropriate substrate in HEPES buffer, pH 7.5 containing 0.01 M $CaCl_2$ and 8% dimethylsulfoxide. The reaction also contains 0.34 mM dithiopyridine which reacts with the thiobenzyl group that is released during hydrolysis and converts it to thiopyridone. The reaction is carried out in an optical cuvette, and the generation of thiopyridone is measured in a spectrophotometer by the absorption produced at 324 nm. The amount of thiopyridone produced in the reaction is proportional to the activity of HUPM.

XI. Production of HUPM Specific Antibodies

HUPM substantially purified using PAGE electrophoresis (see, e.g., Harrington, M. G. (1990) Methods Enzymol. 182:488–495), or other purification techniques, is used to immunize rabbits and to produce antibodies using standard protocols. The HUPM amino acid sequence is analyzed using DNASTAR software (DNASTAR Inc) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester to increase immunogenicity. (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HUPM Using Specific Antibodies

Naturally occurring or recombinant HUPM is substantially purified by immunoaffinity chromatography using antibodies specific for HUPM. An immunoaffinity column is constructed by covalently coupling anti-HUPM antibody to an activated chromatographic resin, such as CNBr-activated Sepharose (Pharmacia & Upjohn). After the coupling, the resin is blocked and washed according to the manufacturer's instructions.

Media containing HUPM are passed over the immunoaffinity column, and the column is washed under conditions that allow the preferential absorbance of HUPM (e.g., high ionic strength buffers in the presence of detergent). The column is eluted under conditions that disrupt antibody/HUPM binding (e.g., a buffer of pH 2 to pH 3, or a high concentration of a chaotrope, such as urea or thiocyanate ion), and HUPM is collected.

XIII. Identification of Molecules Which Interact with HUPM

HUPM, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HUPM, washed, and any wells with labeled HUPM complex are assayed. Data obtained using different concentrations of HUPM are used to calculate values for the number, affinity, and association of HUPM with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated antibody which specifically binds to a polypeptide selected from the group consisting of:
   a) a polypeptide comprising an amino acid sequence of SEQ ID NO:6;
   b) a polypeptide comprising a naturally occurring amino acid sequence at least 90% identical to the amino acid sequence of SEQ ID NO:6;
   c) a biologically active fragment of a polypeptide having at least 90% identity with the amino acid sequence of SEQ ID NO:6; and
   d) an immunogenic fragment of a polypeptide comprising the amino acid sequence of SEQ ID NO:6.

2. A method for diagnosing a condition or disease associated with the expression of human protease molecules (HUPM) in a biological sample, the method comprising:
   a) combining the biological sample with an antibody of claim 1 under conditions suitable for specific binding of the antibody to HUPM; and
   b) detecting specific binding, wherein specific binding correlates with the presence of HUPM in the biological sample.

3. The antibody of claim 1, wherein the antibody is
   a) a chimeric antibody,
   b) a single chain antibody,
   c) a Fab fragment,
   d) a F(ab')$_2$ fragment, or
   e) a humanized antibody.

4. A composition comprising an antibody of claim 1 and an acceptable excipient.

5. A method of diagnosing a condition or disease associated with the expression of HUPM in a subject, comprising:
   a) administering to said subject an effective amount of the composition of claim 4; and
   b) detecting the expression of the HUPM in the subject by detecting the composition of claim 4, wherein the expression of HUPM is associated with the condition or disease.

6. A composition of claim 4, wherein the antibody is labeled.

7. A method of diagnosing a condition or disease associated with the expression of HUPM in a subject, comprising:
   a) administering to said subject an effective amount of the composition of claim 6; and
   b) detecting the expression of the HUPM in the subject by detecting the composition of claim 6, wherein the expression of HUPM is associated with the condition or disease.

8. A method of preparing a polyclonal antibody with the specificity of the antibody of claim 1, the method comprising:
   a) immunizing an animal with a polypeptide having an amino acid sequence of SEQ ID NO: 6 or an immunogenic fragment thereof, under conditions to elicit an antibody response;
   b) isolating antibodies from said animal; and
   c) screening the isolated antibodies with the polypeptide, thereby identifying a polyclonal antibody which binds specifically to a polypeptide having an amino acid sequence of SEQ ID NO:6.

9. An antibody produced by a method of claim 8.

10. A composition comprising the antibody of claim 9 and a suitable carrier.

11. A method of making a monoclonal antibody with the specificity of the antibody of claim 1, the method comprising:
    a) immunizing an animal with a polypeptide having an amino acid sequence of SEQ ID NO: 6, or an immunogenic fragment thereof, under conditions to elicit an antibody response;
    b) isolating antibody producing cells from the animal;
    c) fusing the antibody producing cells with immortalized cells to form monoclonal antibody-producing hybridoma cell;
    d) culturing the hybridoma cells, and
    e) isolating from the culture monoclonal antibody which binds specifically to a polypeptide having an amino acid sequence of SEQ ID NO: 6.

12. A monoclonal antibody produced by a method of claim 11.

13. A composition comprising the antibody of claim 12 and a suitable carrier.

14. The antibody of claim 1, wherein the antibody is produced by screening a Fab expression library.

15. The antibody of claim 1, wherein the antibody is produced by screening a recombinant immunoglobulin library.

16. A method of detecting a polypeptide having an amino acid sequence of SEQ ID NO:6 in a sample, the method comprising:
   a) incubating the antibody of claim 1 with a sample under conditions to allow specific binding of the antibody and the polypeptide, and
   b) detecting specific binding, wherein specific binding indicates the presence of a polypeptide having an amino acid sequence of SEQ ID NO:6 in the sample.

17. A method of purifying a polypeptide having an amino acid sequence of SEQ ID NO:6 from a sample, the method comprising:
   a) incubating the antibody of claim 1 with a sample under conditions to allow specific binding of the antibody and the polypeptide, and
   b) separating the antibody from the sample and obtaining the purified polypeptide having an amino acid sequence of SEQ ID NO:6.

18. An isolated antibody that specifically binds to the polypeptide of SEQ ID NO:6.

19. The isolated antibody of claim 1, wherein the polypeptide has an amino acid sequence of SEQ ID NO:6.

20. The isolated antibody of claim 1, wherein the biological activity is serine protease activity.

21. The isolated antibody of claim 1, wherein the antibody neutralizes a biological activity of SEQ ID NO:6.

22. The isolated antibody of claim 21, wherein the biological activity is serine protease activity.

23. The method of claim 2, wherein HUPM has an amino acid sequence of SEQ ID NO:6.

24. The method of claim 2, wherein the biological sample is a cell or tissue from a mammal.

25. The method of claim 24, wherein the mammal is a human.

26. The method of claim 2, wherein the antibody is labeled.

27. The method of claim 17, wherein the antibody is immobilized on a solid support.

* * * * *

UNITED STATES PATENT AND TRADEMARK OFFICE
CERTIFICATE OF CORRECTION

PATENT NO. : 6,855,811 B2
DATED : February 15, 2005
INVENTOR(S) : Bandman et al.

It is certified that error appears in the above-identified patent and that said Letters Patent is hereby corrected as shown below:

<u>Title page,</u>
Item [56], References Cited, OTHER PUBLICATIONS, at "Blast 2 Sequences…," reference, "http:://" should read -- http:// --; and at "Yousef, G. et al.," reference, "Kalikrein" should read -- Kallikrein --

<u>Column 11,</u>
Line 48, "cDNA." should read -- cDNA, --

<u>Column 12,</u>
Lines 5 and 9, "C." should read -- C --
Line 8, "30° C." should read -- 30° C --

<u>Column 14,</u>
Line 67, "Cat" should read -- C at --

<u>Column 17,</u>
Line 27, "S337" should read -- S357 --

<u>Column 19,</u>
Line 60, "C." should read -- C --

<u>Column 22,</u>
Line 66, "maybe" should read -- may be --

<u>Column 23,</u>
Line 2, "drinpromoter" should read -- drin promoter --

<u>Column 28,</u>
Line 67, "maybe" should read -- may be --

<u>Column 30,</u>
Line 35, "maybe" should read -- may be --

<u>Column 31,</u>
Line 11, "maybe" should read -- may be --

<u>Column 34,</u>
Line 20, "genonuc" should read -- genomic --

UNITED STATES PATENT AND TRADEMARK OFFICE
CERTIFICATE OF CORRECTION

PATENT NO. : 6,855,811 B2
DATED : February 15, 2005
INVENTOR(S) : Bandman et al.

It is certified that error appears in the above-identified patent and that said Letters Patent is hereby corrected as shown below:

Column 38,
Line 19, "maybe" should read -- may be --

Column 41,
Line 56, "for 1 sec" should read -- for 15 sec --

Column 81,
Line 15, at the line ending in 1560, last group "CCTGCCCAGA" should read
-- CCTGCCCACC --
Line 16, at the line ending in 1620, last group "CCTCTGCCCC" should read
-- CCTCTGCCCA --
Line 17, at the line ending in 1680, last group "CCCTCGCACA" should read
-- CCCTCGCAGC --

Column 94,
Line 46, "SEQ ID NO:6," should read -- SEQ ID NO: 6 --

Signed and Sealed this

Ninth Day of August, 2005

JON W. DUDAS
*Director of the United States Patent and Trademark Office*

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
        (A) LENGTH: 63 amino acids
        (B) TYPE: amino acid
        (C) STRANDEDNESS: single
        (D) TOPOLOGY: linear (vii) IMMEDIATE SOURCE:
        (A) LIBRARY: BMARNOT02
        (B) CLONE: 135360

(xi) SEQUENCE DESCRIPTION: SEQ ID NO: 1 :

```
Met Asp Ile Leu Ile Cys Thr Asp Phe Gly Ser Val Asn Tyr Phe
                 5                  10                  15

Asn Val Trp Arg Leu Pro Lys Ser Tyr Leu Ser Leu Phe Tyr Ser
                20                  25                  30

Arg Ile Tyr Ile Val His Asp Glu Val Lys Asp Lys Ala Phe Glu
                35                  40                  45

Leu Glu Leu Ser Trp Val Gly Glu Cys Lys Leu Phe Leu Tyr Ile
                50                  55                  60

Tyr Leu Pro
```

(2) INFORMATION FOR SEQ ID NO: 2:

(i) SEQUENCE CHARACTERISTICS:
        (A) LENGTH: 262 amino acids
        (B) TYPE: amino acid
        (C) STRANDEDNESS: single
        (D) TOPOLOGY: linear (vii) IMMEDIATE SOURCE:
        (A) LIBRARY: TLYMNOT02
        (B) CLONE: 447484

(xi) SEQUENCE DESCRIPTION: SEQ ID NO: 2 :

```
Met Gly Arg Glu Ile Arg Ser Glu Glu Pro Glu Glu Ser Val Pro
                 5                  10                  15

Phe Ser Cys Asp Trp Arg Lys Val Ala Gly Ala Ile Ser Pro Ile
                20                  25                  30

Lys Asp Gln Lys Asn Cys Asn Cys Cys Trp Ala Met Ala Ala Ala
                35                  40                  45

Gly Asn Ile Glu Thr Leu Trp Arg Ile Ser Phe Trp Asp Phe Val
                50                  55                  60

Asp Val Ser Val Gln Glu Leu Leu Asp Cys Gly Arg Cys Gly Asp
```

```
                   65                  70                  75
Gly Cys His Gly Gly Phe Val Trp Asp Ala Phe Ile Thr Val Leu
                80                  85                  90
Asn Asn Ser Gly Leu Ala Ser Glu Lys Asp Tyr Pro Phe Gln Gly
                95                 100                 105
Lys Val Arg Ala His Arg Cys His Pro Lys Lys Tyr Gln Lys Val
               110                 115                 120
Ala Trp Ile Gln Asp Phe Ile Met Leu Gln Asn Asn Glu His Arg
               125                 130                 135
Ile Ala Gln Tyr Leu Ala Thr Tyr Gly Pro Ile Thr Val Thr Ile
               140                 145                 150
Asn Met Lys Pro Leu Gln Leu Tyr Arg Lys Gly Val Ile Lys Ala
               155                 160                 165
Thr Pro Thr Thr Cys Asp Pro Gln Leu Val Asp His Ser Val Leu
               170                 175                 180
Leu Val Gly Phe Gly Ser Val Lys Ser Glu Glu Gly Ile Trp Ala
               185                 190                 195
Glu Thr Val Ser Ser Gln Ser Gln Pro Gln Pro Pro His Pro Thr
               200                 205                 210
Pro Tyr Trp Ile Leu Lys Asn Ser Trp Gly Ala Gln Trp Gly Glu
               215                 220                 225
Lys Gly Tyr Phe Arg Leu His Arg Gly Ser Asn Thr Cys Gly Ile
               230                 235                 240
Thr Lys Phe Pro Leu Thr Ala Arg Val Gln Lys Pro Asp Met Lys
               245                 250                 255
Pro Arg Val Ser Cys Pro Pro
               260

(2) INFORMATION FOR SEQ ID NO: 3:

(i) SEQUENCE CHARACTERISTICS:
        (A) LENGTH: 314 amino acids
        (B) TYPE: amino acid
        (C) STRANDEDNESS: single
        (D) TOPOLOGY: linear (vii) IMMEDIATE SOURCE:
        (A) LIBRARY: PROSTUT03
        (B) CLONE: 789927

(xi) SEQUENCE DESCRIPTION: SEQ ID NO: 3 :

Met Gly Ala Arg Gly Ala Leu Leu Leu Ala Leu Leu Leu Ala Arg
                 5                  10                  15
Ala Gly Leu Arg Lys Pro Glu Ser Gln Glu Ala Ala Pro Leu Ser
                20                  25                  30
Gly Pro Cys Gly Arg Arg Val Ile Thr Ser Arg Ile Val Gly Gly
                35                  40                  45
Glu Asp Ala Glu Leu Gly Arg Trp Pro Trp Gln Gly Ser Leu Arg
                50                  55                  60
Leu Trp Asp Ser His Val Cys Gly Val Ser Leu Leu Ser His Arg
                65                  70                  75
Trp Ala Leu Thr Ala Ala His Cys Phe Glu Thr Tyr Ser Asp Leu
                80                  85                  90
Ser Asp Pro Ser Gly Trp Met Val Gln Phe Gly Gln Leu Thr Ser
                95                 100                 105
Met Pro Ser Phe Trp Ser Leu Gln Ala Tyr Tyr Thr Arg Tyr Phe
               110                 115                 120
```

-continued

```
Val Ser Asn Ile Tyr Leu Ser Pro Arg Tyr Leu Gly Asn Ser Pro
            125                 130                 135

Tyr Asp Ile Ala Leu Val Lys Leu Ser Ala Pro Val Thr Tyr Thr
            140                 145                 150

Lys His Ile Gln Pro Ile Cys Leu Gln Ala Ser Thr Phe Glu Phe
            155                 160                 165

Glu Asn Arg Thr Asp Cys Trp Val Thr Gly Trp Gly Tyr Ile Lys
            170                 175                 180

Glu Asp Glu Ala Leu Pro Ser Pro His Thr Leu Gln Glu Val Gln
            185                 190                 195

Val Ala Ile Ile Asn Asn Ser Met Cys Asn His Leu Phe Leu Lys
            200                 205                 210

Tyr Ser Phe Arg Lys Asp Ile Phe Gly Asp Met Val Cys Ala Gly
            215                 220                 225

Asn Ala Gln Gly Gly Lys Asp Ala Cys Phe Gly Asp Ser Gly Gly
            230                 235                 240

Pro Leu Ala Cys Asn Lys Asn Gly Leu Trp Tyr Gln Ile Gly Val
            245                 250                 255

Val Ser Trp Gly Val Gly Cys Gly Arg Pro Asn Arg Pro Gly Val
            260                 265                 270

Tyr Thr Asn Ile Ser His His Phe Glu Trp Ile Gln Lys Leu Met
            275                 280                 285

Ala Gln Ser Gly Met Ser Gln Pro Asp Pro Ser Trp Pro Leu Leu
            290                 295                 300

Phe Phe Pro Leu Leu Trp Ala Leu Pro Leu Leu Gly Pro Val
            305                 310
```

(2) INFORMATION FOR SEQ ID NO: 4:

(i) SEQUENCE CHARACTERISTICS:
        (A) LENGTH: 420 amino acids
        (B) TYPE: amino acid
        (C) STRANDEDNESS: single
        (D) TOPOLOGY: linear (vii) IMMEDIATE SOURCE:
        (A) LIBRARY: LUNGAST01
        (B) CLONE: 877617

(xi) SEQUENCE DESCRIPTION: SEQ ID NO: 4 :

```
Met Ser Pro Pro Leu Leu Gln Pro Leu Leu Leu Leu Leu Leu Pro
              5                  10                  15

Leu Leu Asn Val Glu Pro Ser Gly Ala Thr Leu Ile Arg Ile Pro
             20                  25                  30

Leu His Arg Val Gln Pro Gly Arg Arg Thr Leu Asn Leu Leu Arg
             35                  40                  45

Gly Trp Arg Glu Pro Ala Glu Leu Pro Lys Leu Gly Ala Pro Ser
             50                  55                  60

Pro Gly Asp Lys Pro Ile Phe Val Pro Leu Ser Asn Tyr Arg Asp
             65                  70                  75

Val Gln Tyr Phe Gly Glu Ile Gly Leu Gly Thr Pro Pro Gln Asn
             80                  85                  90

Phe Thr Val Ala Phe Asp Thr Gly Ser Ser Asn Leu Trp Val Pro
             95                 100                 105

Ser Arg Arg Cys His Phe Phe Ser Val Pro Cys Trp Leu His His
            110                 115                 120
```

```
Arg Phe Asp Pro Lys Ala Ser Ser Phe Gln Ala Asn Gly Thr
            125                 130                 135

Lys Phe Ala Ile Gln Tyr Gly Thr Gly Arg Val Asp Gly Ile Leu
            140                 145                 150

Ser Glu Asp Lys Leu Thr Ile Gly Gly Ile Lys Gly Ala Ser Val
            155                 160                 165

Ile Phe Gly Glu Ala Leu Trp Glu Pro Ser Leu Val Phe Ala Phe
            170                 175                 180

Ala His Phe Asp Gly Ile Leu Gly Leu Gly Phe Pro Ile Leu Ser
            185                 190                 195

Val Glu Gly Val Arg Pro Pro Met Asp Val Leu Val Glu Gln Gly
            200                 205                 210

Leu Leu Asp Lys Pro Val Phe Ser Phe Tyr Leu Asn Arg Asp Pro
            215                 220                 225

Glu Glu Pro Asp Gly Gly Glu Leu Val Leu Gly Gly Ser Asp Pro
            230                 235                 240

Ala His Tyr Ile Pro Pro Leu Thr Phe Val Pro Val Thr Val Pro
            245                 250                 255

Ala Tyr Trp Gln Ile His Met Glu Arg Val Lys Val Gly Pro Gly
            260                 265                 270

Leu Thr Leu Cys Ala Lys Gly Cys Ala Ala Ile Leu Asp Thr Gly
            275                 280                 285

Thr Ser Leu Ile Thr Gly Pro Thr Glu Glu Ile Arg Ala Leu His
            290                 295                 300

Ala Ala Ile Gly Gly Ile Pro Leu Leu Ala Gly Glu Tyr Ile Ile
            305                 310                 315

Leu Cys Ser Glu Ile Pro Lys Leu Pro Ala Val Ser Phe Leu Leu
            320                 325                 330

Gly Gly Val Trp Phe Asn Leu Thr Ala His Asp Tyr Val Ile Gln
            335                 340                 345

Thr Thr Arg Asn Gly Val Arg Leu Cys Leu Ser Gly Phe Gln Ala
            350                 355                 360

Leu Asp Val Pro Pro Ala Gly Pro Phe Trp Ile Leu Gly Asp
            365                 370                 375

Val Phe Leu Gly Thr Tyr Val Ala Val Phe Asp Arg Gly Asp Met
            380                 385                 390

Lys Ser Ser Ala Arg Val Gly Leu Ala Arg Ala Arg Thr Arg Gly
            395                 400                 405

Ala Asp Leu Gly Trp Gly Glu Thr Ala Gln Ala Gln Phe Pro Gly
            410                 415                 420

(2) INFORMATION FOR SEQ ID NO: 5:

(i) SEQUENCE CHARACTERISTICS:
        (A) LENGTH: 200 amino acids
        (B) TYPE: amino acid
        (C) STRANDEDNESS: single
        (D) TOPOLOGY: linear (vii) IMMEDIATE SOURCE:
        (A) LIBRARY: KIDNTUT01
        (B) CLONE: 999322

(xi) SEQUENCE DESCRIPTION: SEQ ID NO: 5 :

Met Cys Glu Leu Met Tyr His Leu Gly Glu Pro Ser Leu Ala Gly
              5                  10                  15

Gln Arg Leu Ile Gln Asp Asp Met Leu Cys Ala Gly Ser Val Gln
```

-continued

```
                        20                  25                  30
Gly Lys Lys Asp Ser Cys Gln Val Thr Ala Ala Pro Gly His Pro
                35                  40                  45
Ile Gln Leu Cys Gly Pro Phe Arg Leu Thr Leu Ser Trp Thr Phe
                50                  55                  60
Ser Pro Cys Pro Thr Pro Gln Gly Leu Gln Arg Asp Gln Ser Pro
                65                  70                  75
Cys Leu Ala Pro Trp Pro Gln Leu Ile Leu Glu Gly Thr Trp
                80                  85                  90
Gly Pro Gly Val Ser Leu Asn Ala Asp Leu Met Gly Pro Ser Leu
                95                 100                 105
Ser Leu Pro Gln Gly Asp Ser Gly Pro Leu Val Cys Pro Ile
               110                 115                 120
Asn Asp Thr Trp Ile Gln Ala Gly Ile Val Ser Trp Gly Phe Gly
               125                 130                 135
Cys Ala Arg Pro Phe Arg Pro Gly Val Tyr Thr Gln Val Leu Ser
               140                 145                 150
Tyr Thr Asp Trp Ile Gln Arg Thr Leu Ala Glu Ser His Ser Gly
               155                 160                 165
Met Ser Gly Ala Arg Pro Gly Ala Pro Gly Ser His Ser Gly Thr
               170                 175                 180
Ser Arg Ser His Pro Val Leu Leu Leu Glu Leu Leu Thr Val Cys
               185                 190                 195
Leu Leu Gly Ser Leu
               200

(2) INFORMATION FOR SEQ ID NO: 6:

(i) SEQUENCE CHARACTERISTICS:
        (A) LENGTH: 435 amino acids
        (B) TYPE: amino acid
        (C) STRANDEDNESS: single
        (D) TOPOLOGY: linear (vii) IMMEDIATE SOURCE:
        (A) LIBRARY: COLNNOT13
        (B) CLONE: 1337018

(xi) SEQUENCE DESCRIPTION: SEQ ID NO: 6 :

Met Asp Pro Asp Ser Asp Gln Pro Leu Asn Ser Leu Asp Val Lys
                 5                  10                  15
Pro Leu Arg Lys Pro Arg Ile Pro Met Glu Thr Phe Arg Lys Val
                20                  25                  30
Gly Ile Pro Ile Ile Ile Ala Leu Leu Ser Leu Ala Ser Ile Ile
                35                  40                  45
Ile Val Val Val Leu Ile Lys Val Ile Leu Asp Lys Tyr Tyr Phe
                50                  55                  60
Leu Cys Gly Gln Pro Leu His Phe Ile Pro Arg Lys Gln Leu Cys
                65                  70                  75
Asp Gly Glu Leu Asp Cys Pro Leu Gly Glu Asp Glu His Cys
                80                  85                  90
Val Lys Ser Phe Pro Glu Gly Pro Ala Val Ala Val Arg Leu Ser
                95                 100                 105
Lys Asp Arg Ser Thr Leu Gln Val Leu Asp Ser Ala Thr Gly Asn
               110                 115                 120
Trp Phe Ser Ala Cys Phe Asp Asn Phe Thr Glu Ala Leu Ala Glu
               125                 130                 135
```

```
Thr Ala Cys Arg Gln Met Gly Tyr Ser Ser Lys Pro Thr Phe Arg
            140                 145                 150

Ala Val Glu Ile Gly Pro Asp Gln Asp Leu Asp Val Val Glu Ile
            155                 160                 165

Thr Glu Asn Ser Gln Glu Leu Arg Met Arg Asn Ser Ser Gly Pro
            170                 175                 180

Cys Leu Ser Gly Ser Leu Val Ser Leu His Cys Leu Ala Cys Gly
            185                 190                 195

Glu Ser Leu Lys Thr Pro Arg Val Val Gly Gly Glu Glu Ala Ser
            200                 205                 210

Val Asp Ser Trp Pro Trp Gln Val Ser Ile Gln Tyr Asp Lys Gln
            215                 220                 225

His Val Cys Gly Gly Ser Ile Leu Asp Pro His Trp Val Leu Thr
            230                 235                 240

Ala Ala His Cys Phe Arg Lys His Thr Asp Val Phe Asn Trp Lys
            245                 250                 255

Val Arg Ala Gly Ser Asp Lys Leu Gly Ser Phe Pro Ser Leu Ala
            260                 265                 270

Val Ala Lys Ile Ile Ile Glu Phe Asn Pro Met Tyr Pro Lys
            275                 280                 285

Asp Asn Asp Ile Ala Leu Met Lys Leu Gln Phe Pro Leu Thr Phe
            290                 295                 300

Ser Gly Thr Val Arg Pro Ile Cys Leu Pro Phe Phe Asp Glu Glu
            305                 310                 315

Leu Thr Pro Ala Thr Pro Leu Trp Ile Ile Gly Trp Gly Phe Thr
            320                 325                 330

Lys Gln Asn Gly Gly Lys Met Ser Asp Ile Leu Leu Gln Ala Ser
            335                 340                 345

Val Gln Val Ile Asp Ser Thr Arg Cys Asn Ala Asp Asp Ala Tyr
            350                 355                 360

Gln Gly Glu Val Thr Glu Lys Met Met Cys Ala Gly Ile Pro Glu
            365                 370                 375

Gly Gly Val Asp Thr Cys Gln Gly Asp Ser Gly Gly Pro Leu Met
            380                 385                 390

Tyr Gln Ser Asp Gln Trp His Val Val Gly Ile Val Ser Trp Gly
            395                 400                 405

Tyr Gly Cys Gly Gly Pro Ser Thr Pro Gly Val Tyr Thr Lys Val
            410                 415                 420

Ser Ala Tyr Leu Asn Trp Ile Tyr Asn Val Trp Lys Ala Glu Leu
            425                 430                 435

(2) INFORMATION FOR SEQ ID NO: 7:

(i) SEQUENCE CHARACTERISTICS:
        (A) LENGTH: 260 amino acids
        (B) TYPE: amino acid
        (C) STRANDEDNESS: single
        (D) TOPOLOGY: linear (vii) IMMEDIATE SOURCE:
        (A) LIBRARY: COLNNOT27
        (B) CLONE: 1798496

(xi) SEQUENCE DESCRIPTION: SEQ ID NO: 7 :

Met Gly Arg Pro Arg Pro Arg Ala Ala Lys Thr Trp Met Phe Leu
             5                  10                  15
```

-continued

```
Leu Leu Leu Gly Gly Ala Trp Ala Gly His Ser Arg Ala Gln Glu
             20              25                  30

Asp Lys Val Leu Gly Gly His Glu Cys Gln Pro His Ser Gln Pro
             35              40                  45

Trp Gln Ala Ala Leu Ser Gln Gly Gln Gln Leu Leu Cys Gly Gly
             50              55                  60

Val Leu Val Gly Gly Asn Trp Val Leu Thr Ala Ala His Cys Lys
             65              70                  75

Lys Pro Lys Tyr Thr Val Arg Leu Gly Asp His Ser Leu Gln Asn
             80              85                  90

Lys Asp Gly Pro Glu Gln Glu Ile Pro Val Val Gln Ser Ile Pro
             95             100                 105

His Pro Cys Tyr Asn Ser Ser Asp Val Glu Asp His Asn His Asp
            110             115                 120

Leu Met Leu Leu Gln Leu Arg Asp Gln Ala Ser Leu Gly Ser Lys
            125             130                 135

Val Lys Pro Ile Ser Leu Ala Asp His Cys Thr Gln Pro Gly Gln
            140             145                 150

Lys Cys Thr Val Ser Gly Trp Gly Thr Val Thr Ser Pro Arg Glu
            155             160                 165

Asn Phe Pro Asp Thr Leu Asn Cys Ala Glu Val Lys Ile Phe Pro
            170             175                 180

Gln Lys Lys Cys Glu Asp Ala Tyr Pro Gly Gln Ile Thr Asp Gly
            185             190                 195

Met Val Cys Ala Gly Ser Ser Lys Gly Ala Asp Thr Cys Gln Gly
            200             205                 210

Asp Ser Gly Gly Pro Leu Val Cys Asp Gly Ala Leu Gln Gly Ile
            215             220                 225

Thr Ser Trp Gly Ser Asp Pro Cys Gly Arg Ser Asp Lys Pro Gly
            230             235                 240

Val Tyr Thr Asn Ile Cys Arg Tyr Leu Asp Trp Ile Lys Lys Ile
            245             250                 255

Ile Gly Ser Lys Gly
            260

(2) INFORMATION FOR SEQ ID NO: 8:

(i) SEQUENCE CHARACTERISTICS:
        (A) LENGTH: 175 amino acids
        (B) TYPE: amino acid
        (C) STRANDEDNESS: single
        (D) TOPOLOGY: linear (vii) IMMEDIATE SOURCE:
        (A) LIBRARY: UTRSNOT08
        (B) CLONE: 2082147

(xi) SEQUENCE DESCRIPTION: SEQ ID NO: 8 :

Met Ala Gln Ser Gln Gly Trp Val Lys Arg Tyr Ile Lys Ala Phe
              5              10                  15

Cys Lys Gly Phe Phe Val Ala Val Pro Val Ala Val Thr Phe Leu
             20              25                  30

Asp Arg Val Ala Cys Val Ala Arg Val Glu Gly Ala Ser Met Gln
             35              40                  45

Pro Ser Leu Asn Pro Gly Gly Ser Gln Ser Ser Asp Val Val Leu
             50              55                  60

Leu Asn His Trp Lys Val Arg Asn Phe Glu Val His Arg Gly Asp
```

-continued

```
                     65                   70                   75
Ile Val Ser Leu Val Ser Pro Lys Asn Pro Glu Gln Lys Ile Ile
                     80                   85                   90

Lys Arg Val Ile Ala Leu Glu Gly Asp Ile Val Arg Thr Ile Gly
                     95                  100                  105

His Lys Asn Arg Tyr Val Lys Val Pro Arg Gly His Ile Trp Val
                    110                  115                  120

Glu Gly Asp His His Gly His Ser Phe Asp Ser Asn Ser Phe Gly
                    125                  130                  135

Pro Val Ser Leu Gly Leu Leu His Ala His Ala Thr His Ile Leu
                    140                  145                  150

Trp Pro Pro Glu Arg Trp Gln Lys Leu Glu Ser Val Leu Pro Pro
                    155                  160                  165

Glu Arg Leu Pro Val Gln Arg Glu Glu Glu
                    170                  175
```

(2) INFORMATION FOR SEQ ID NO: 9:

(i) SEQUENCE CHARACTERISTICS:
        (A) LENGTH: 519 amino acids
        (B) TYPE: amino acid
        (C) STRANDEDNESS: single
        (D) TOPOLOGY: linear (vii) IMMEDIATE SOURCE:
        (A) LIBRARY: ENDCNOT03
        (B) CLONE: 2170967

(xi) SEQUENCE DESCRIPTION: SEQ ID NO: 9 :

```
Met Phe Leu Leu Pro Leu Pro Ala Ala Gly Arg Val Val Arg
                      5                   10                   15

Arg Leu Ala Val Arg Arg Phe Gly Ser Arg Ser Leu Ser Thr Ala
                     20                   25                   30

Asp Met Thr Lys Gly Leu Val Leu Gly Ile Tyr Ser Lys Glu Lys
                     35                   40                   45

Glu Asp Asp Val Pro Gln Phe Thr Ser Ala Gly Glu Asn Phe Asp
                     50                   55                   60

Lys Leu Leu Ala Gly Lys Leu Arg Glu Thr Leu Asn Ile Ser Gly
                     65                   70                   75

Pro Pro Leu Lys Ala Gly Lys Thr Arg Thr Phe Tyr Gly Leu His
                     80                   85                   90

Gln Asp Phe Pro Ser Val Val Leu Val Gly Leu Gly Lys Lys Ala
                     95                  100                  105

Ala Gly Ile Asp Glu Gln Glu Asn Trp His Glu Gly Lys Glu Asn
                    110                  115                  120

Ile Arg Ala Ala Val Ala Ala Gly Cys Arg Gln Ile Gln Asp Leu
                    125                  130                  135

Glu Leu Ser Ser Val Glu Val Asp Pro Cys Gly Asp Ala Gln Ala
                    140                  145                  150

Ala Ala Glu Gly Ala Val Leu Gly Leu Tyr Glu Tyr Asp Asp Leu
                    155                  160                  165

Lys Gln Lys Lys Lys Met Ala Val Ser Ala Lys Leu Tyr Gly Ser
                    170                  175                  180

Gly Asp Gln Glu Ala Trp Gln Lys Gly Val Leu Phe Ala Ser Gly
                    185                  190                  195

Gln Asn Leu Ala Arg Gln Leu Met Glu Thr Pro Ala Asn Glu Met
                    200                  205                  210
```

-continued

```
Thr Pro Thr Arg Phe Ala Glu Ile Ile Glu Lys Asn Leu Lys Ser
            215                 220                 225

Ala Ser Ser Lys Thr Glu Val His Ile Arg Pro Lys Ser Trp Ile
            230                 235                 240

Glu Glu Gln Ala Met Gly Ser Phe Leu Ser Val Ala Lys Gly Ser
            245                 250                 255

Asp Glu Pro Pro Val Phe Leu Glu Ile His Tyr Lys Gly Ser Pro
            260                 265                 270

Asn Ala Asn Glu Pro Pro Leu Val Phe Val Gly Lys Gly Ile Thr
            275                 280                 285

Phe Asp Ser Gly Gly Ile Ser Ile Lys Ala Ser Ala Asn Met Asp
            290                 295                 300

Leu Met Arg Ala Asp Met Gly Gly Ala Ala Thr Ile Cys Ser Ala
            305                 310                 315

Ile Val Ser Ala Ala Lys Leu Asn Leu Pro Ile Asn Ile Ile Gly
            320                 325                 330

Leu Ala Pro Leu Cys Glu Asn Met Pro Ser Gly Lys Ala Asn Lys
            335                 340                 345

Pro Gly Asp Val Val Arg Ala Lys Asn Gly Lys Thr Ile Gln Val
            350                 355                 360

Asp Asn Thr Asp Ala Glu Gly Arg Leu Ile Leu Ala Asp Ala Leu
            365                 370                 375

Cys Tyr Ala His Thr Phe Asn Pro Lys Val Ile Leu Asn Ala Ala
            380                 385                 390

Thr Leu Thr Gly Ala Met Asp Val Ala Leu Gly Ser Gly Ala Thr
            395                 400                 405

Gly Val Phe Thr Asn Ser Ser Trp Leu Trp Asn Lys Leu Phe Glu
            410                 415                 420

Ala Ser Ile Glu Thr Gly Asp Arg Val Trp Arg Met Pro Leu Phe
            425                 430                 435

Glu His Tyr Thr Arg Gln Val Val Asp Cys Gln Leu Ala Asp Val
            440                 445                 450

Asn Asn Ile Gly Lys Tyr Arg Ser Ala Gly Ala Cys Thr Ala Ala
            455                 460                 465

Ala Phe Leu Lys Glu Phe Val Thr His Pro Lys Trp Ala His Leu
            470                 475                 480

Asp Ile Ala Gly Val Met Thr Asn Lys Asp Glu Val Pro Tyr Leu
            485                 490                 495

Arg Lys Gly Met Thr Gly Arg Pro Thr Arg Thr Leu Ile Glu Phe
            500                 505                 510

Leu Leu Arg Phe Ser Gln Asp Asn Ala
            515
```

(2) INFORMATION FOR SEQ ID NO: 10:

(i) SEQUENCE CHARACTERISTICS:
        (A) LENGTH: 327 amino acids
        (B) TYPE: amino acid
        (C) STRANDEDNESS: single
        (D) TOPOLOGY: linear (vii) IMMEDIATE SOURCE:
        (A) LIBRARY: SMCANOT01
        (B) CLONE: 2484218

(xi) SEQUENCE DESCRIPTION: SEQ ID NO: 10 :

```
Met Ala Ala Ala Ala Ala Ala Ala Thr Asn Gly Thr Gly
                5                  10                 15

Gly Ser Ser Gly Met Glu Val Asp Ala Val Val Pro Ser Val
                20              25                 30

Met Ala Cys Gly Val Thr Gly Ser Val Ser Val Ala Leu His Pro
                35              40                 45

Leu Val Ile Leu Asn Ile Ser Asp His Trp Ile Arg Met Arg Ser
            50              55                    60

Gln Glu Gly Arg Pro Val Gln Val Ile Gly Ala Leu Ile Gly Lys
            65                  70                    75

Gln Glu Gly Arg Asn Ile Glu Val Met Asn Ser Phe Glu Leu Leu
            80                  85                    90

Ser His Thr Val Glu Glu Lys Ile Ile Ile Asp Lys Glu Tyr Tyr
            95                  100                   105

Tyr Thr Lys Glu Glu Gln Phe Lys Gln Val Phe Lys Glu Leu Glu
            110                 115                   120

Phe Leu Gly Trp Tyr Thr Thr Gly Gly Pro Pro Asp Pro Ser Asp
            125                 130                   135

Ile His Val His Lys Gln Val Cys Glu Ile Glu Ser Pro Leu
            140                 145                150

Phe Leu Lys Leu Asn Pro Met Thr Lys His Thr Asp Leu Pro Val
            155                 160                   165

Ser Val Phe Glu Ser Val Ile Asp Ile Ile Asn Gly Glu Ala Thr
            170                 175                   180

Met Leu Phe Ala Glu Leu Thr Tyr Thr Leu Ala Thr Glu Glu Ala
            185                 190                   195

Glu Arg Ile Gly Val Asp His Val Ala Arg Met Thr Ala Thr Gly
            200                 205                   210

Ser Gly Glu Asn Ser Thr Val Ala Glu His Leu Ile Ala Gln His
            215                 220                   225

Ser Ala Ile Lys Met Leu His Ser Arg Val Lys Leu Ile Leu Glu
            230                 235                   240

Tyr Val Lys Ala Ser Glu Ala Gly Glu Val Pro Phe Asn His Glu
            245                 250                   255

Ile Leu Arg Glu Ala Tyr Ala Leu Cys His Cys Leu Pro Val Leu
            260                 265                   270

Ser Thr Asp Lys Phe Lys Thr Asp Phe Tyr Asp Gln Cys Asn Asp
            275                 280                   285

Val Gly Leu Met Ala Tyr Leu Gly Thr Ile Thr Lys Thr Cys Asn
            290                 295                   300

Thr Met Asn Gln Phe Val Asn Lys Phe Asn Val Leu Tyr Asp Arg
            305                 310                   315

Gln Gly Ile Gly Arg Arg Met Arg Gly Leu Phe Phe
            320                 325
```

(2) INFORMATION FOR SEQ ID NO: 11:

(i) SEQUENCE CHARACTERISTICS:
        (A) LENGTH: 458 amino acids
        (B) TYPE: amino acid
        (C) STRANDEDNESS: single
        (D) TOPOLOGY: linear (vii) IMMEDIATE SOURCE:
        (A) LIBRARY: SINIUCT01
        (B) CLONE: 2680548

(xi) SEQUENCE DESCRIPTION: SEQ ID NO: 11 :

```
Met Ala Ala Pro Arg Ala Gly Arg Gly Ala Gly Trp Ser Leu Arg
                 5                  10                  15
Ala Trp Arg Ala Leu Gly Gly Ile Arg Trp Gly Arg Pro Arg
             20                  25                  30
Leu Thr Pro Asp Leu Arg Ala Leu Leu Thr Ser Gly Thr Ser Asp
                 35                  40                  45
Pro Arg Ala Arg Val Thr Tyr Gly Thr Pro Ser Leu Trp Ala Arg
                 50                  55                  60
Leu Ser Val Gly Val Thr Glu Pro Arg Ala Cys Leu Thr Ser Gly
                 65                  70                  75
Thr Pro Gly Pro Arg Ala Gln Leu Thr Ala Val Thr Pro Asp Thr
                 80                  85                  90
Arg Thr Arg Glu Ala Ser Glu Asn Ser Gly Thr Arg Ser Arg Ala
                 95                  100                 105
Trp Leu Ala Val Ala Leu Gly Ala Gly Gly Ala Val Leu Leu Leu
                 110                 115                 120
Leu Trp Gly Gly Gly Arg Gly Pro Pro Ala Val Leu Ala Ala Val
                 125                 130                 135
Pro Ser Pro Pro Pro Ala Ser Pro Arg Ser Gln Tyr Asn Phe Ile
                 140                 145                 150
Ala Asp Val Val Glu Lys Thr Ala Pro Ala Val Val Tyr Ile Glu
                 155                 160                 165
Ile Leu Asp Arg His Pro Phe Leu Gly Arg Glu Val Pro Ile Ser
                 170                 175                 180
Asn Gly Ser Gly Phe Val Val Ala Ala Asp Gly Leu Ile Val Thr
                 185                 190                 195
Asn Ala His Val Val Ala Asp Arg Arg Val Arg Val Arg Leu
                 200                 205                 210
Leu Ser Gly Asp Thr Tyr Glu Ala Val Val Thr Ala Val Asp Pro
                 215                 220                 225
Val Ala Asp Ile Ala Thr Leu Arg Ile Gln Thr Lys Glu Pro Leu
                 230                 235                 240
Pro Thr Leu Pro Leu Gly Arg Ser Ala Asp Val Arg Gln Gly Glu
                 245                 250                 255
Phe Val Val Ala Met Gly Ser Pro Phe Ala Leu Gln Asn Thr Ile
                 260                 265                 270
Thr Ser Gly Ile Val Ser Ser Ala Gln Arg Pro Ala Arg Asp Leu
                 275                 280                 285
Gly Leu Pro Gln Thr Asn Val Glu Tyr Ile Gln Thr Asp Ala Ala
                 290                 295                 300
Ile Asp Phe Gly Asn Ser Gly Gly Pro Leu Val Asn Leu Asp Gly
                 305                 310                 315
Glu Val Ile Gly Val Asn Thr Met Lys Val Thr Ala Gly Ile Ser
                 320                 325                 330
Phe Ala Ile Pro Ser Asp Arg Leu Arg Glu Phe Leu His Arg Gly
                 335                 340                 345
Glu Lys Lys Asn Ser Ser Ser Gly Ile Ser Gly Ser Gln Arg Arg
                 350                 355                 360
Tyr Ile Gly Val Met Met Leu Thr Leu Ser Pro Ser Ile Leu Ala
                 365                 370                 375
Glu Leu Gln Leu Arg Glu Pro Ser Phe Pro Asp Val Gln His Gly
                 380                 385                 390
```

```
Val Leu Ile His Lys Val Ile Leu Gly Ser Pro Ala His Arg Ala
                395                 400                 405

Gly Leu Arg Pro Gly Asp Val Ile Leu Ala Ile Gly Glu Gln Met
                410                 415                 420

Val Gln Asn Ala Glu Asp Val Tyr Glu Ala Val Arg Thr Gln Ser
                425                 430                 435

Gln Leu Ala Val Gln Ile Arg Arg Gly Arg Glu Thr Leu Thr Leu
                440                 445                 450

Tyr Val Thr Pro Glu Val Thr Glu
                455
```

(2) INFORMATION FOR SEQ ID NO: 12:

(i) SEQUENCE CHARACTERISTICS:
        (A) LENGTH: 532 amino acids
        (B) TYPE: amino acid
        (C) STRANDEDNESS: single
        (D) TOPOLOGY: linear (vii) IMMEDIATE SOURCE:
        (A) LIBRARY: KIDNFET01
        (B) CLONE: 2957969

(xi) SEQUENCE DESCRIPTION: SEQ ID NO: 12 :

```
Met Leu Gly Ala Trp Ala Gly Arg Lys Met Ala Asn Val Gly Leu
                 5                  10                  15

Gln Phe Gln Ala Ser Ala Gly Asp Ser Asp Pro Gln Ser Arg Pro
                20                  25                  30

Leu Leu Leu Leu Gly Gln Leu His His Leu His Arg Val Pro Trp
                35                  40                  45

Ser His Val Arg Gly Lys Leu Gln Pro Arg Val Thr Glu Glu Leu
                50                  55                  60

Trp Gln Ala Ala Leu Ser Thr Leu Asn Pro Asn Pro Thr Asp Ser
                65                  70                  75

Cys Pro Leu Tyr Leu Asn Tyr Ala Thr Val Ala Ala Leu Pro Cys
                80                  85                  90

Arg Val Ser Arg His Asn Ser Pro Ser Ala Ala His Phe Ile Thr
                95                 100                 105

Arg Leu Val Arg Thr Cys Leu Pro Pro Gly Ala His Arg Cys Ile
                110                 115                 120

Val Met Val Cys Glu Gln Pro Glu Val Phe Ala Ser Ala Cys Ala
                125                 130                 135

Leu Ala Arg Ala Phe Pro Leu Phe Thr His Arg Ser Gly Ala Ser
                140                 145                 150

Arg Arg Leu Glu Lys Lys Thr Val Thr Val Glu Phe Phe Leu Val
                155                 160                 165

Gly Gln Asp Asn Gly Pro Val Glu Val Ser Thr Leu Gln Cys Leu
                170                 175                 180

Ala Asn Ala Thr Asp Gly Val Arg Leu Ala Ala Arg Ile Val Asp
                185                 190                 195

Thr Pro Cys Asn Glu Met Asn Thr Asp Thr Phe Leu Glu Glu Ile
                200                 205                 210

Asn Lys Val Gly Lys Glu Leu Gly Ile Ile Pro Thr Ile Ile Arg
                215                 220                 225

Asp Glu Glu Leu Lys Thr Arg Gly Phe Gly Gly Ile Tyr Gly Val
                230                 235                 240
```

-continued

```
Gly Lys Ala Ala Leu His Pro Pro Ala Leu Ala Val Leu Ser His
            245                 250                 255

Thr Pro Asp Gly Ala Thr Gln Thr Ile Ala Trp Val Gly Lys Gly
            260                 265                 270

Ile Val Tyr Asp Thr Gly Gly Leu Ser Ile Lys Gly Lys Thr Thr
            275                 280                 285

Met Pro Gly Met Lys Arg Asp Cys Gly Gly Ala Ala Ala Val Leu
            290                 295                 300

Gly Ala Phe Arg Ala Ala Ile Lys Gln Gly Phe Lys Asp Asn Leu
            305                 310                 315

His Ala Val Phe Cys Leu Ala Glu Asn Ser Val Gly Pro Asn Ala
            320                 325                 330

Thr Arg Pro Asp Asp Ile His Leu Leu Tyr Ser Gly Lys Thr Val
            335                 340                 345

Glu Ile Asn Asn Thr Asp Ala Glu Gly Arg Leu Val Leu Ala Asp
            350                 355                 360

Gly Val Ser Tyr Ala Cys Lys Asp Leu Gly Ala Asp Ile Ile Leu
            365                 370                 375

Asp Met Ala Thr Leu Thr Gly Ala Gln Gly Ile Ala Thr Gly Lys
            380                 385                 390

Tyr His Ala Ala Val Leu Thr Asn Ser Ala Glu Trp Glu Ala Ala
            395                 400                 405

Cys Val Lys Ala Gly Arg Lys Cys Gly Asp Leu Val His Pro Leu
            410                 415                 420

Val Tyr Cys Pro Glu Leu His Phe Ser Glu Phe Thr Ser Ala Val
            425                 430                 435

Ala Asp Met Lys Asn Ser Val Ala Asp Arg Asp Asn Ser Pro Ser
            440                 445                 450

Ser Cys Ala Gly Leu Phe Ile Ala Ser His Ile Gly Phe Asp Trp
            455                 460                 465

Pro Gly Val Trp Val His Leu Asp Ile Ala Ala Pro Val His Ala
            470                 475                 480

Gly Glu Arg Ala Thr Gly Phe Gly Val Ala Leu Leu Leu Ala Leu
            485                 490                 495

Phe Gly Arg Ala Ser Glu Asp Pro Leu Leu Asn Leu Val Ser Pro
            500                 505                 510

Leu Gly Cys Glu Val Asp Val Glu Glu Gly Asp Val Gly Arg Asp
            515                 520                 525

Ser Lys Arg Arg Arg Leu Val
            530

(2) INFORMATION FOR SEQ ID NO: 13:

(i) SEQUENCE CHARACTERISTICS:
        (A) LENGTH: 1542 base pairs
        (B) TYPE: nucleic acid
        (C) STRANDEDNESS: single
        (D) TOPOLOGY: linear (vii) IMMEDIATE SOURCE:
        (A) LIBRARY: BMARNOT02
        (B) CLONE: 135360

(xi) SEQUENCE DESCRIPTION: SEQ ID NO: 13 :

ATATTCTAAA AGGGCACAGT TAATGACGCC TCTTCCTAGT GAATCCGTGT TCTTTATGAG      60

GTATCTTTTA TAGTTGTATC TTTTTTTTTT TCTGAGATGG AGTCTCGCTC TACTGTAGCC     120
```

```
CAGGATGGAG TGCAGTAGTG TGATCTTGGC TCACTGCAAC CCCTGCCTCC CGGGTTCAAG    180

GAATTCTCCT GCCTTAGCCT CCTGAGTAGC TGAGATTACA GGCGCCCACC ACCACACCTG    240

GCTGATTTTT GTTTCTTAGT AGAGACAGGG TTTCACCATG TTGGCCAGGC TAGTCTCGAA    300

CTGACCTCAA GTGATCCATC CGCCTTGGTC TCCCAAAGTG TTGGGATTAC AGGTGTGAGC    360

CACTGTGCCC AGCCAAGTTA TATCTCTAAA GCAATGTGCA AAATAAACT  GAACTTGGGT    420

TGATTAGGTA TATTCAACAT TTGTCGGGAG AGTAGATGTT TCATTTTATT TCAGTCCCTG    480

TGTAATTTGT CTTCTCTAAT GTTAAATACT ATGTAGAATG TGTCTGTGTA ATTTTATAGA    540

TACTTTTATT ATGGATGGAC ATTCTAATTT GTACTGACTT TGGGTCTGTG AACTACTTCA    600

ATGTTTGGAG GTTACCAAAA TCTTACCTTT CCCTTTTCTA TTCTAGAATT TACATAGTAC    660

ATGACGAAGT TAAGGATAAA GCTTTTGAAC TAGAACTCAG CTGGGTTGGT GAATGTAAGT    720

TATTTTTGTA CATTTATTTG CCTTAGGAAT GATCTGTACC ACAGCTAATT TACAACTGAG    780

TGTCCTTTCT AATATAATGA AAGCTAAAGC AAATTTACTA GGTTGTCTAA TGAAGGGAAA    840

GTTCTGCTTA ATAATTGACT TAAGTTGTGA ACACGTTATT TTTTGAAACA TCCATTTCAT    900

GGTTTTAAGA TACTATGCTA TAAATTAATG CTCAGGATTA TAAATAGCA  TAATTTACTT    960

TCATTTCCAT AAGAACTTAA TATGTAGGCA CATATAATCT CATGTAGAAG CAGCACACAA   1020

AAATATTCGA GTATTACTCA TAGTACAACT TTGCAACCTT AGGTGAGTCA GATATGTGGA   1080

TTGGGTAGAT CCTATGGTAT ACTGCAAGTT ACAATATGGT ACTCAATTTA AAATTCATTT   1140

ACACATGTGG CTTAATTTAC AGTAACTAAT GGAAGACATG AAATTGTTCC AAAAGATATA   1200

AGAGAAGAAG CAGAGAAATA TGCTAAGGTA AGCCACAGCA CAAAAACTTC TCTTGGCCAG   1260

GTACAGTCAG GGAATCTCTT AGCCCAGGAG TTTGAGACCA GCCTGAGCAG CACAGCAAGA   1320

CCCCCATCCC TAATTTAAAA AAAAAAAAAT TCTCTAACCA AAATTATGTG TTGAATAATA   1380

TAAATAGACT GGGGTGGTTT CTATGAAATA ACACTGAGAG TTCAGTTGAA CTAAAGATAG   1440

AAATTTTCTA GGTTATCTCT AGTGGGTAAA GTTGCCTTGG TTCCAAAAAA AAAAAACTTG   1500

GGAGGTTTAG ACTGCAAAGA GTTTTTTAGG ACTTCTAATA CT                      1542

(2) INFORMATION FOR SEQ ID NO: 14:

(i) SEQUENCE CHARACTERISTICS:
        (A) LENGTH: 3043 base pairs
        (B) TYPE: nucleic acid
        (C) STRANDEDNESS: single
        (D) TOPOLOGY: linear (vii) IMMEDIATE SOURCE:
        (A) LIBRARY: TLYMNOT02
        (B) CLONE: 447484

(xi) SEQUENCE DESCRIPTION: SEQ ID NO: 14 :

CCCACGCGTC CGGTAAATGG CTGTAATACA GGAATTTTGC CACAACCAGT TGGGACAGTC     60

TTGTTGCAAA TACCAGAACC TCAAGAATCG AACAGTGACG CAGGAATAAA TTTAATAGCC    120

CTTCCAGCAT TTTCACAGGT GGACCCTGAG GTATTTGCTG CCCTTCCTGC TGAACTTCAG    180

AGGGAGCTGA AAGCAGCGTA TGATCAAAGA CAAAGGCAGG GCGAGAACAG CACTCACCAG    240

CAGTCAGCCA GCGCATCTGT GCCAAAGAAT CCTTTACTTC ATCTAAAGGC AGCAGTGAAA    300

GAAAAGAAAA GAAACAAGAA GAAAAAAACC ATTGGTTCAC CAAAAAGGAT TCAGAGTCCT    360

TTGAATAACA AGCTGCTTAA CAGTCCTGCA AAAACTCTGC CAGGGGCCTG TGGCAGTCCC    420

CAGAAGTTAA TTGATGGGTT TCTAAAACAT GAAGGACCTC CTGCAGAGAA ACCCCTGGAA    480
```

| | |
|---|---|
| GAACTCTCTG CTTCTACTTC AGGTGTGCCA GGCCTTTCTA GTTTGCAGTC TGACCCAGCT | 540 |
| GGCTGTGTGA GACCTCCAGC ACCCAATCTA GCTGGAGCTG TTGAATTCAA TGATGTGAAG | 600 |
| ACCTTGCTCA GAGAATGGAT AACTACAATT TCAGATCCAA TGGAAGAAGA CATTCTCCAA | 660 |
| GTTGTGAAAT ACTGTACTGA TCTAATAGAA GAAAAGATT TGGAAAAACT GGATCTAGTT | 720 |
| ATAAAATACA TGAAAAGGCT GATGCAGCAA TCGGTGGAAT CGGTTTGGAA TATGGCATTT | 780 |
| GACTTTATTC TTGACAATGT CCAGGTGGTT TTACAACAAA CTTATGGAAG CACATTAAAA | 840 |
| GTTACATAAA TATTACCAGA GAGCCTGATG CTCTCTGATA GCTGTGCCAT AAGTGCTTGT | 900 |
| GAGGTATTTG CAAAGTGCAT GATAGTAATG CTCGGAGTTT TTATAATTTT AAATTTCTTT | 960 |
| TAAAGCAAGT GTTTTGTACA TTTCTTTTCA AAAAGTGCCA AATTTGTCAG TATTGCATGT | 1020 |
| AAATAATTGT GTTAATTATT TTACTGTAGC ATAGATTCTA TTTACAAAAT GTTTGTTTAT | 1080 |
| AAAGTTTTAT GGATTTTTAC AGTGAAGTGT TTACAGTTGT TTAATAAAGA ACTGTATGTA | 1140 |
| TATTTTGTAC AGGCTCCTTT TTGTGAATCC TTAAAAACTC AACTCTAGGA AGCAACTACT | 1200 |
| GTTTATTATA CTAAAAGGCT GAAAAACCTC CAGGCCAGAC TGCTAAGCTC TGAAATTCCT | 1260 |
| GAGAGGTCTC AGACCGGGAT TCTACTTGTT CCAAGAAAGG GTAAAGCTTC TAAACCATCT | 1320 |
| TATTCTTGTC TCCAAGCATG AACACAGGAG CATGTTAAGA AAATCTTTAC TACTTCTTCC | 1380 |
| ATGCGGAGAA ATCTACATAT TTTGAATTAG AAACACCCTC ACACCCACTT GAAGATTTTT | 1440 |
| TTCCTGGGAA CATTATGTCC CGTAGATCAG AGGTGGTGTT GTCTTTTTGC TTCTACTGGC | 1500 |
| CATTGAGAAA CTTTGATGAT AAAAAAGAAC GGTATAGATT TTTCAAACGT ATATAAAATA | 1560 |
| TTTTTATGTT ATATGTTATG CCATAACTTT AAAATAAAAA TAGTTTAAAA TTCTATGCTA | 1620 |
| GTGGATATTT GGAACTTTTT CCTCAAACAA ACACCCCACA CTGACTTCAG CAAAACCCTA | 1680 |
| AAACTAGCTA CAGATTACTG CTACGAATGA ATCATTAAGT TTTGTGTCTG CAACAATTTA | 1740 |
| GAAGCACTAA GCCCAAATAT CAGGAAATGT GTGTATGATG GAATTTTCTA GGACAAAACA | 1800 |
| GATCAAGATT AAAACAGATC AAGATTAATG TATAAAAATG TCTACTAAAA CAGATCAAGA | 1860 |
| TTAAAACAGA TCAAGATTAA TGTATAAAAA CTCTACTGT TACCAGGTGC TGGCATACAA | 1920 |
| GGTAGTGTGA TGATAGTTTA GTTTGTAAGA TAATTCTTGT CCTAGGAGGA CAACTTGTGG | 1980 |
| GAGAGAAGCT ACACTAACAT GGAAGCCTAA CAGAGCTTGC TTACTGGTGG ATGTCTGTTT | 2040 |
| TCTTTATTGG TAGTTTGGTT TAGAATTGTG ATGATTACAA TGGACTCGTG ACTACACAAG | 2100 |
| CAGTAAAAAG CAGCCAGCTC TATGGCTATC GGAGGGCAGC TGGAGGGGTC CCCAGCATGG | 2160 |
| GCAGAGAAAT AAGGTCTGAA GAGCCAGAGG AGTCAGTACC TTTCAGCTGT GACTGGCGGA | 2220 |
| AGGTGGCCGG CGCCATCTCA CCCATCAAGG ACCAGAAAAA CTGCAACTGC TGCTGGGCCA | 2280 |
| TGGCAGCGGC AGGCAACATA GAGACCCTGT GGCGCATCAG TTTCTGGGAT TTTGTGGACG | 2340 |
| TCTCCGTGCA GGAACTGCTG GACTGTGGCC GCTGTGGGGA TGGCTGCCAC GGTGGCTTCG | 2400 |
| TCTGGGACGC GTTCATAACT GTCCTCAACA ACAGCGGCCT GGCCAGTGAA AAGGACTACC | 2460 |
| CGTTCCAGGG CAAAGTCAGA GCCCACAGGT GCCACCCCAA GAAGTACCAG AAGGTGGCCT | 2520 |
| GGATCCAGGA CTTCATCATG CTGCAGAACA ACGAGCACAC AATTGCGCAG TACCTGGCCA | 2580 |
| CTTATGGCCC CATCACCGTG ACCATCAACA TGAAGCCCCT TCAGCTATAC CGGAAAGGTG | 2640 |
| TGATCAAGGC CACACCCACC ACCTGTGACC CCCAGCTTGT GGACCACTCT GTCCTGCTGG | 2700 |
| TGGGTTTTGG CAGCGTCAAG TCAGAGGAGG GGATATGGGC AGAGACAGTC TCATCGCAGT | 2760 |
| CTCAGCCTCA GCCTCCACAC CCCACCCCAT ACTGGATCCT GAAGAACTCC TGGGGGGCCC | 2820 |
| AATGGGGAGA GAAGGGCTAT TTCCGGCTGC ACCGAGGGAG CAATACCTGT GGCATCACCA | 2880 |

| | |
|---|---|
| AGTTCCCGCT CACTGCCCGT GTGCAGAAAC CGGATATGAA GCCCCGAGTC TCCTGCCCTC | 2940 |
| CCTGAACCCA CCTGGCCCCC TCAGCTCTGT CCTGTTAGGC CAACTGCCTC CTTGCCAGCC | 3000 |
| CCACCCCCAG GTTTTTGCCC ATCCTCCCAA TCTCAATACA GGG | 3043 |

(2) INFORMATION FOR SEQ ID NO: 15:

(i) SEQUENCE CHARACTERISTICS:
        (A) LENGTH: 1081 base pairs
        (B) TYPE: nucleic acid
        (C) STRANDEDNESS: single
        (D) TOPOLOGY: linear (vii) IMMEDIATE SOURCE:
        (A) LIBRARY: PROSTUT03
        (B) CLONE: 789927

(xi) SEQUENCE DESCRIPTION: SEQ ID NO: 15 :

| | |
|---|---|
| AGGAGGCAGA GGGGGCGTCA GGCCGCGGGA GAGGAGGCCA TGGGCGCGCG CGGGGCGCTG | 60 |
| CTGCTGGCGC TGCTGCTGGC TCGGGCTGGA CTCAGGAAGC CGGAGTCGCA GGAGGCGGCG | 120 |
| CCCTTATCAG GACCATGCGG CCGACGGGTC ATCACGTCGC GCATCGTGGG TGGAGAGGAC | 180 |
| GCCGAACTCG GGCGTTGGCC GTGGCAGGGG AGCCTGCGCC TGTGGGATTC CCACGTATGC | 240 |
| GGAGTGAGCC TGCTCAGCCA CCGCTGGGCA CTCACGGCGG CGCACTGCTT TGAAACCTAT | 300 |
| AGTGACCTTA GTGATCCCTC CGGGTGGATG GTCCAGTTTG CCAGCTGAC TTCCATGCCA | 360 |
| TCCTTCTGGA GCCTGCAGGC CTACTACACC CGTTACTTCG TATCGAATAT CTATCTGAGC | 420 |
| CCTCGCTACC TGGGGAATTC ACCCTATGAC ATTGCCTTGG TGAAGCTGTC TGCACCTGTC | 480 |
| ACCTACACTA AACACATCCA GCCCATCTGT CTCCAGGCCT CCACATTTGA GTTTGAGAAC | 540 |
| CGGACAGACT GCTGGGTGAC TGGCTGGGGG TACATCAAAG AGGATGAGGC ACTGCCATCT | 600 |
| CCCCACACCC TCCAGGAAGT TCAGGTCGCC ATCATAAACA ACTCTATGTG CAACCACCTC | 660 |
| TTCCTCAAGT ACAGTTTCCG CAAGGACATC TTTGGAGACA TGGTTTGTGC TGGCAATGCC | 720 |
| CAAGGCGGGA AGGATGCCTG CTTCGGTGAC TCAGGTGGAC CCTTGGCCTG TAACAAGAAT | 780 |
| GGACTGTGGT ATCAGATTGG AGTCGTGAGC TGGGGAGTGG GCTGTGGTCG GCCCAATCGG | 840 |
| CCCGGTGTCT ACACCAATAT CAGCCACCAC TTTGAGTGGA TCCAGAAGCT GATGGCCCAG | 900 |
| AGTGGCATGT CCCAGCCAGA CCCCTCCTGG CCACTACTCT TTTTCCCTCT TCTCTGGGCT | 960 |
| CTCCCACTCC TGGGGCCGGT CTGAGCCTAC CTGAGCCCAT GCAGCCTGGG GCCACTGCCA | 1020 |
| AGTCAGGCCC TGGTTCTCTT CTGTCTTGTT TGGTAATAAA CACATTCCAG TTGATGCCTG | 1080 |
| C | 1081 |

(2) INFORMATION FOR SEQ ID NO: 16:

(i) SEQUENCE CHARACTERISTICS:
        (A) LENGTH: 2061 base pairs
        (B) TYPE: nucleic acid
        (C) STRANDEDNESS: single
        (D) TOPOLOGY: linear (vii) IMMEDIATE SOURCE:
        (A) LIBRARY: LUNGAST01
        (B) CLONE: 877617

(xi) SEQUENCE DESCRIPTION: SEQ ID NO: 16 :

| | |
|---|---|
| CTTGAGAGCT CTCAAATACT TGGTCATGGA TGAAGCCGAC CGAATACTGA ATATGGATTT | 60 |
| TGAGACAGAG GTTGACAAGC CTCGAGATCG GAAAACATTC CTCTTCTCTG CCACCATGAC | 120 |

-continued

| | |
|---|---|
| CAAGAAGGTT CAAAAACTTC AGCGAGCAGC TCTGAAGAAT CCTGTGAAAT GTGCCGTTTC | 180 |
| CTCTAAATAC CAGACAGTTG AAAAATTACA GCAATATTAT ATTTTTATTC CCTCTAAATT | 240 |
| CAAGGATACC TACCTGGTTT ATATTCTAAA TGAATTGGCT GGAAACTCCT TTATGATATT | 300 |
| CTGCAGCACC TGTAATAATA CCCAGAGAAC AGCTTTGCTA CTGCGAAATC TTGGCTTCAC | 360 |
| TGCCATCCCC CTCCATGGAC AAATGAGTCA GAGTAAGCGC CTAGGATCCC TTAATAAGTT | 420 |
| TAAGGCCAAG GCCCGTTCCA TTCTTCTAGC AACTGACGTT GCCAGCCGAG GTTTGGACAT | 480 |
| ACCTCATGTA GATGTGGTTG TCAACTTTGA CATTCCTACC CATTCCAAGG ATTACATCCA | 540 |
| TCGAGTAGGT CGAACAGCTA GAGCTGGGCG CTCCGGAAAG GCTATTACTT TTGTCACACA | 600 |
| GTATGATGTG GAACTCTTCC AGCGCATAGA ACACTTAATT GGGAAGAAAC TACCAGGTTT | 660 |
| TCCAACACAG GATGATGAGG TTATGATGCT GACAGAACGC GTCCCCAGCG ATGTCTCCAC | 720 |
| CACCGCTGCT GCAACCCCTG CTGCTGCTGC TGCCTCTGCT GAATGTGGAG CCTTCCGGGG | 780 |
| CCACACTGAT CCGCATCCCT CTTCATCGAG TCCAACCTGG ACGCAGGACC CTGAACCTAC | 840 |
| TGAGGGGATG GAGAGAACCA GCAGAGCTCC CCAAGTTGGG GGCCCCATCC CCTGGGGACA | 900 |
| AGCCCATCTT CGTACCTCTC TCGAACTACA GGGATGTGCA GTATTTTGGG GAAATTGGGC | 960 |
| TGGGAACGCC TCCACAAAAC TTCACTGTTG CCTTTGACAC TGGCTCCTCC AATCTCTGGG | 1020 |
| TCCCGTCCAG GAGATGCCAC TTCTTCAGTG TGCCCTGCTG GTTACACCAC CGATTTGATC | 1080 |
| CCAAAGCCTC TAGCTCCTTC CAGGCCAATG GGACCAAGTT TGCCATTCAA TATGGAACTG | 1140 |
| GGCGGGTAGA TGGAATCCTG AGCGAGGACA AGCTGACTAT TGGTGGAATC AAGGGTGCAT | 1200 |
| CAGTGATTTT CGGGGAGGCT CTCTGGGAGC CCAGCCTGGT CTTCGCTTTT GCCCATTTTG | 1260 |
| ATGGGATATT GGGCCTCGGT TTTCCCATTC TGTCTGTGGA AGGAGTTCGG CCCCCGATGG | 1320 |
| ATGTACTGGT GGAGCAGGGG CTATTGGATA AGCCTGTCTT CTCCTTTTAC CTCAACAGGG | 1380 |
| ACCCTGAAGA GCCTGATGGA GGAGAGCTGG TCCTGGGGGG CTCGGACCCG GCACACTACA | 1440 |
| TCCCACCCCT CACCTTCGTG CCAGTCACGG TCCCTGCCTA CTGGCAGATC CACATGGAGC | 1500 |
| GTGTGAAGGT GGGCCCAGGG CTGACTCTCT GTGCCAAGGG CTGTGCTGCC ATCCTGGATA | 1560 |
| CGGGCACGTC CCTCATCACA GGACCCACTG AGGAGATCCG GGCCCTGCAT GCAGCCATTG | 1620 |
| GGGGAATCCC CTTGCTGGCT GGGGAGTACA TCATCCTGTG CTCGGAAATC CCAAAGCTCC | 1680 |
| CCGCAGTCTC CTTCCTTCTT GGGGGGGTCT GGTTTAACCT CACGGCCCAT GATTACGTCA | 1740 |
| TCCAGACTAC TCGAAATGGC GTCCGCCTCT GCTTGTCCGG TTTCCAGGCC CTGGATGTCC | 1800 |
| CTCCGCCTGC AGGGCCCTTC TGGATCCTCG GTGACGTCTT CTTGGGGACG TATGTGGCCG | 1860 |
| TCTTCGACCG CGGGGACATG AAGAGCAGCG CCCGGGTGGG CCTGGCGCGC GCTCGCACTC | 1920 |
| GCGGAGCGGA CCTCGGATGG GGAGAGACTG CGCAGGCGCA GTTCCCCGGG TGACGCCCAA | 1980 |
| GTGAAGCGCA TGCGCAGCGG GTGGTCGCGG AGGTCCTGCT ACCCAGTAAA AATCCACTAT | 2040 |
| TTCCATTGAA AAAAAAAAA A | 2061 |

(2) INFORMATION FOR SEQ ID NO: 17:

(i) SEQUENCE CHARACTERISTICS:
        (A) LENGTH: 1186 base pairs
        (B) TYPE: nucleic acid
        (C) STRANDEDNESS: single
        (D) TOPOLOGY: linear (vii) IMMEDIATE SOURCE:
        (A) LIBRARY: KIDNTUT01
        (B) CLONE: 999322

(xi) SEQUENCE DESCRIPTION: SEQ ID NO: 17 :

| | | | | | |
|---|---|---|---|---|---|
| TAAGCGTCGC | CAGACCAGCC | TGAGTGGTCT | CACAGACGTT | GGTCTGCGTG | TTTATCTCCT | 60 |
| CTCCCCTCCC | ACCCCACCCT | GAAGCTGGGA | ACACTTGGGG | CCAGGACCCA | TGCTGTCCAG | 120 |
| ACTGTGGGAC | TCCCCTTGGC | CAAGGTGACC | ACCATATTGG | ATTTTGGGGA | TCTTGAGCCA | 180 |
| GTGTCCAGGA | TTGTGCCCGT | GTTGGGATGA | ATAAGCCAAG | GCTAAGAGGT | CATGAGATTA | 240 |
| GCCAGGGTCA | TGGGAGAGGA | TCTGGGCTTG | AGCCCTGCTC | CCTGACCCCA | CTGCCTCCTG | 300 |
| GTTTGGGAGT | TGAGAAGAGC | AGGGTGGGTG | GGCAGAGAAG | AGGTAGGAGG | TGCAGGCTGC | 360 |
| CGCCATCACA | GGTGAGAGGG | CAGAGGCTCA | CCTGATGGGG | ACGAGGCTTG | AGGTGGGCTC | 420 |
| AGGCTGGCCC | CCACATCACA | TCCAGCCCTG | GCGAGTGTCC | TTCAGGAGGT | GGCTGTGCCC | 480 |
| CTCCTGGACT | CGAACATGTG | TGAGCTGATG | TACCACCTAG | GAGAGCCCAG | CCTGGCTGGC | 540 |
| CAGCGCCTCA | TCCAGGACGA | CATGCTCTGT | GCTGGCTCTG | TCCAGGGCAA | GAAAGACTCC | 600 |
| TGCCAGGTGA | CTGCAGCTCC | TGGTCACCCC | ATCCAGTTGT | GTGGGCCCTT | TAGGCTCACC | 660 |
| CTGTCCTGGA | CTTTCTCCCC | ATGTCCCACA | CCTCAGGGTC | TCCAGAGGGA | CCAGAGTCCT | 720 |
| TGCCTAGCTC | CTTGGCCTCA | GCAGCTGATT | CTCGAAGGCA | CTTGGGGCCC | AGGTGTCTCC | 780 |
| CTCAATGCAG | ACCTCATGGG | GCCCTCCCTC | TCTCTCCCCC | AGGGTGACTC | CGGGGGGCCG | 840 |
| CTGGTCTGCC | CCATCAATGA | TACGTGGATC | CAGGCCGGCA | TTGTGAGCTG | GGGATTCGGC | 900 |
| TGTGCCCGGC | CTTTCCGGCC | TGGTGTCTAC | ACCCAGGTGC | TAAGCTACAC | AGACTGGATT | 960 |
| CAGAGAACCC | TGGCTGAATC | TCACTCAGGC | ATGTCTGGGG | CCCGCCCAGG | TGCCCCAGGA | 1020 |
| TCCCACTCAG | GCACCTCCAG | ATCCCACCCA | GTGCTGCTGC | TTGAGCTGTT | GACCGTATGC | 1080 |
| TTGCTTGGGT | CCCTGTGAAC | CATGAGCCAT | GGAGTCCGGG | ATCCCCTTTC | TGGTAGGATT | 1140 |
| GATGGAATCT | AATAATAAAA | ACTGTAGGTT | TTTTATGTGT | AAAAAC | | 1186 |

(2) INFORMATION FOR SEQ ID NO: 18:

(i) SEQUENCE CHARACTERISTICS:
        (A) LENGTH: 2038 base pairs
        (B) TYPE: nucleic acid
        (C) STRANDEDNESS: single
        (D) TOPOLOGY: linear (vii) IMMEDIATE SOURCE:
        (A) LIBRARY: COLNNOT13
        (B) CLONE: 1337018

(xi) SEQUENCE DESCRIPTION: SEQ ID NO: 18:

| | | | | | |
|---|---|---|---|---|---|
| GCAGCTTGCT | CAGCGGACAA | GGATGCTGGG | CGTGAGGGAC | CAAGGCCTGC | CCTGCACTCG | 60 |
| GGCCTCCTCC | AGCCAGTGCT | GACCAGGGAC | TTCTGACCTG | CTGGCCAGCC | AGGACCTGTG | 120 |
| TGGGGAGGCC | CTCCTGCTGC | CTTGGGGTGA | CAATCTCAGC | TCCAGGCTAC | AGGGAGACCG | 180 |
| GGAGGATCAC | AGAGCCAGCA | TGGATCCTGA | CAGTGATCAA | CCTCTGAACA | GCCTCGATGT | 240 |
| CAAACCCCTG | CGCAAACCCC | GTATCCCCAT | GGAGACCTTC | AGAAAGGTGG | GGATCCCCAT | 300 |
| CATCATAGCA | CTACTGAGCC | TGGCGAGTAT | CATCATTGTG | GTTGTCCTCA | TCAAGGTGAT | 360 |
| TCTGGATAAA | TACTACTTCC | TCTGCGGGCA | GCCTCTCCAC | TTCATCCCGA | GGAAGCAGCT | 420 |
| GTGTGACGGA | GAGCTGGACT | GTCCCTTGGG | GGAGGACGAG | GAGCACTGTG | TCAAGAGCTT | 480 |
| CCCCGAAGGG | CCTGCAGTGG | CAGTCCGCCT | CTCCAAGGAC | CGATCCACAC | TGCAGGTGCT | 540 |
| GGACTCGGCC | ACAGGGAACT | GGTTCTCTGC | CTGTTTCGAC | AACTTCACAG | AAGCTCTCGC | 600 |
| TGAGACAGCC | TGTAGGCAGA | TGGGCTACAG | CAGCAAACCC | ACTTTCAGAG | CTGTGGAGAT | 660 |

-continued

```
TGGCCCAGAC CAGGATCTGG ATGTTGTTGA AATCACAGAA AACAGCCAGG AGCTTCGCAT      720

GCGGAACTCA AGTGGGCCCT GTCTCTCAGG CTCCCTGGTC TCCCTGCACT GTCTTGCCTG      780

TGGGGAGAGC CTGAAGACCC CCCGTGTGGT GGGTGGGGAG GAGGCCTCTG TGGATTCTTG      840

GCCTTGGCAG GTCAGCATCC AGTACGACAA ACAGCACGTC TGTGGAGGGA GCATCCTGGA      900

CCCCCACTGG GTCCTCACGG CAGCCCACTG CTTCAGGAAA CATACCGATG TGTTCAACTG      960

GAAGGTGCGG GCAGGCTCAG ACAAACTGGG CAGCTTCCCA TCCCTGGCTG TGGCCAAGAT     1020

CATCATCATT GAATTCAACC CCATGTACCC CAAAGACAAT GACATCGCCC TCATGAAGCT     1080

GCAGTTCCCA CTCACTTTCT CAGGCACAGT CAGGCCCATC TGTCTGCCCT TCTTTGATGA     1140

GGAGCTCACT CCAGCCACCC CACTCTGGAT CATTGGATGG GGCTTTACGA AGCAGAATGG     1200

AGGGAAGATG TCTGACATAC TGCTGCAGGC GTCAGTCCAG GTCATTGACA GCACACGGTG     1260

CAATGCAGAC GATGCGTACC AGGGGAAGT CACCGAGAAG ATGATGTGTG CAGGCATCCC     1320

GGAAGGGGGT GTGGACACCT GCCAGGGTGA CAGTGGTGGG CCCCTGATGT ACCAATCTGA     1380

CCAGTGGCAT GTGGTGGGCA TCGTTAGCTG GGGCTATGGC TGCGGGGGCC CGAGCACCCC     1440

AGGAGTATAC ACCAAGGTCT CAGCCTATCT CAACTGGATC TACAATGTCT GGAAGGCTGA     1500

GCTGTAATGC TGCTGCCCCT TTGCAGTGCT GGGAGCCGCT TCCTTCCTGC CCTGCCCAGA     1560

TGGGGATCCC CCAAAGTCAG ACACAGAGCA AGAGTCCCCT TGGGTACACC CCTCTGCCCC     1620

CAGCCTCAGC ATTTCTTGGA GCAGCAAAGG GCCTCAATTC CTATAAGAGA CCCTCGCACA     1680

CCAGAGGCGC CCAGAGGAAG TCAGCAGCCC TAGCTCGGCC ACACTTGGTG CTCCCAGCAT     1740

CCCAGGGAGA GACACAGCCC ACTGAACAAG GTCTCAGGGG TATTGCTAAG CCAAGAAGGA     1800

ACTTTCCCAC ACTACTGAAT GGAAGCAGGG TGTCTTGTAA AAGCCCAGAT CACTGTGGGC     1860

TGGAGAGGAG AAGGAAAGGG TCTGCGCCAG CCCTGTCCGT CTTCACCCAT CCCCAAGCCT     1920

ACTAGAGCAA GAAACCAGTT GTAATATAAA ATGCACTGCC CTACTGTTGG TATGACTACC     1980

GTTACCTACT GTTGTCATTG TTATTACAGC TATGGCCACT ATTATTAAAG AGCTGTGA       2038
```

(2) INFORMATION FOR SEQ ID NO: 19:

(i) SEQUENCE CHARACTERISTICS:
        (A) LENGTH: 994 base pairs
        (B) TYPE: nucleic acid
        (C) STRANDEDNESS: single
        (D) TOPOLOGY: linear (vii) IMMEDIATE SOURCE:
        (A) LIBRARY: COLNNOT27
        (B) CLONE: 1798496

(xi) SEQUENCE DESCRIPTION: SEQ ID NO: 19 :

```
GTGCAGGAGG AGAAGGAGGA GGAGCAGGAG GTGGAGATTC CCAGTTAAAA GGCTCCAGAA       60

TCGTGTACCA GGCAGAGAAC TGAAGTACTG GGGCCTCCTC CACTGGGTCC GAATCAGTAG      120

GTGACCCCGC CCCTGGATTC TGGAAGACCT CACCATGGGA CGCCCCGAC CTCGTGCGGC      180

CAAGACGTGG ATGTTCCTGC TCTTGCTGGG GGGAGCCTGG GCAGGACACT CCAGGGCACA      240

GGAGGACAAG GTGCTGGGGG GTCATGAGTG CCAACCCCAT TCGCAGCCTT GGCAGGCGGC      300

CTTGTCCCAG GGCCAGCAAC TACTCTGTGG CGGTGTCCTT GTAGGTGGCA ACTGGGTCCT      360

TACAGCTGCC CACTGTAAAA AACCGAAATA CACAGTACGC CTGGGAGACC ACAGCCTACA      420

GAATAAAGAT GGCCCAGAGC AAGAAATACC TGTGGTTCAG TCCATCCCAC ACCCCTGCTA      480

CAACAGCAGC GATGTGGAGG ACCACAACCA TGATCTGATG CTTCTTCAAC TGCGTGACCA      540
```

```
GGCATCCCTG GGGTCCAAAG TGAAGCCCAT CAGCCTGGCA GATCATTGCA CCCAGCCTGG      600

CCAGAAGTGC ACCGTCTCAG GCTGGGGCAC TGTCACCAGT CCCCGAGAGA ATTTTCCTGA      660

CACTCTCAAC TGTGCAGAAG TAAAAATCTT TCCCCAGAAG AAGTGTGAGG ATGCTTACCC      720

GGGGCAGATC ACAGATGGCA TGGTCTGTGC AGGCAGCAGC AAAGGGGCTG ACACGTGCCA      780

GGGCGATTCT GGAGGCCCCC TGGTGTGTGA TGGTGCACTC CAGGGCATCA CATCCTGGGG      840

CTCAGACCCC TGTGGGAGGT CCGACAAACC TGGCGTCTAT ACCAACATCT GCCGCTACCT      900

GGACTGGATC AAGAAGATCA TAGGCAGCAA GGGCTGATTC TAGGATAAGC ACTAGATCTC      960

CCTTAATAAA CTCACAACTC TCTGAAAAAA AAAA                                  994

(2) INFORMATION FOR SEQ ID NO: 20:

(i) SEQUENCE CHARACTERISTICS:
        (A) LENGTH: 1318 base pairs
        (B) TYPE: nucleic acid
        (C) STRANDEDNESS: single
        (D) TOPOLOGY: linear (vii) IMMEDIATE SOURCE:
        (A) LIBRARY: UTRSNOT08
        (B) CLONE: 2082147

(xi) SEQUENCE DESCRIPTION: SEQ ID NO: 20 :

TCTGAGGCGC GTGCGCGGCC ACCCCAGCCT AGTCCTCTTC TTGGTGCCAC TGGCTAACTA       60

GGTTGAGAAA CCGGCGCCAC AGGCGCANCA CCTGGCCCGG AGCTGGCCCG CTCCTCCCCG      120

CCGAGCCGCC CCCAACAACG CGCCCTCTCC CAGTCCTCAC AAAGGGGCCT AGTCCGGCCC      180

CCGGCTCTGG CCGTGAGGGA GCGCTGTGGG GGCGCGCTGC CTTCTGCCTG GAAGTGTTGG      240

GCAGGTGGTG GGAGAGCGTC AGGCTTGAAC AACATGATTT TAAAGCACGT GTCTGTCTGT      300

CGTTTTTTAC TTTTAGGGTT TTGGCCAAAT TGGGCGAGGG CACAAAATAA CCACTTACCC      360

CTTCTCACCG AGGAAGAGCG GGAGAAAGGG TATGGCACAG TCACAAGGGT GGGTGAAAAG      420

ATACATCAAG GCCTTTTGTA AAGGCTTCTT TGTGGCGGTG CCTGTGGCAG TGACTTTCTT      480

GGATCGGGTC GCCTGTGTGG CAAGAGTAGA AGGAGCATCG ATGCAGCCTT CTTTGAATCC      540

TGGGGGGAGC CAGTCATCTG ATGTGGTGCT TTTGAACCAC TGGAAAGTGA GGAATTTTGA      600

AGTACACCGT GGTGACATTG TATCATTGGT GTCTCCTAAA AACCCAGAAC AGAAGATCAT      660

TAAGAGAGTG ATTGCTCTTG AAGGAGATAT TGTCAGAACC ATAGGACACA AAAACCGGTA      720

TGTCAAAGTC CCCCGTGGTC ACATCTGGGT TGAAGGTGAT CATCATGGAC ACAGTTTTGA      780

CAGTAATTCT TTTGGGCCGG TTTCCCTAGG ACTTCTGCAT GCCCATGCCA CACATATCCT      840

GTGGCCCCCA GAGCGCTGGC AGAAATTGGA ATCTGTTCTT CCTCCAGAGC GCTTACCAGT      900

ACAGAGAGAA GAGGAATGAC TGCATGAATC TACCTGAGTT GCTGGCATTG GGAGGCCAGT      960

TACTGGAAAG GAATGGAAAA AAGAAGCCTC CAAAAGGGAA AAACTTCTGA CAATATGATG     1020

CTGTGCGAGA ATATTTACA GCACATTAAA ACGATCTGTA TTATTAAATA AATAATTTTC     1080

AAATGTTAAA CAGTATTAAA TGGCACCTGA TTTTGTGTTA AATTTTAGTT CCCTGTTGTT     1140

TAATGCCCCC AAAATATGCA GACCTTTGGG AATATAAAAA TATTGCACCC ACATGTCTTA     1200

ATGGGGCTGA ATTTCAGATT ATTTGTTACA TATACTTATT ATATTGATTG TTGGGTTTTG     1260

ATTTTGGTGC TTGCTGCTGA AATAAATTGA AAATTAATAT TCAAAAAAAA AAAAAAG        1318

(2) INFORMATION FOR SEQ ID NO: 21:

(i) SEQUENCE CHARACTERISTICS:
```

(A) LENGTH: 2136 base pairs
        (B) TYPE: nucleic acid
        (C) STRANDEDNESS: single
        (D) TOPOLOGY: linear (vii) IMMEDIATE SOURCE:
        (A) LIBRARY: ENDCNOT03
        (B) CLONE: 2170967

(xi) SEQUENCE DESCRIPTION: SEQ ID NO: 21 :

```
GGCTCTTTTA AATGACCCCA GGCGTCGTGT ATTGAATCCT AGACTCACGT CCGTCTCGCC      60

GGCGCCCGAG CCAGTCCGCG CGCACCGCGT CTGCGTCCCC GAAAGCCCCG CCCGCAAGGG     120

CTGCCCTGCC TACCTGGTCT CCGACGTGCT CGTCTGGAGG GCGGTGCGAG GGGCCGAGCC     180

GACAAGATGT TCTTGCTGCC TCTTCCGGCT GCGGGGCGAG TAGTCGTCCG ACGTCTGGCC     240

GTGAGACGTT TCGGGAGCCG GAGTCTCTCC ACCGCAGACA TGACGAAGGG CCTTGTTTTA     300

GGAATCTATT CCAAAGAAAA AGAAGATGAT GTGCCACAGT TCACAAGTGC AGGAGAGAAT     360

TTTGATAAAT TGTTAGCTGG AAAGCTGAGA GAGACTTTGA ACATATCTGG ACCACCTCTG     420

AAGGCAGGGA AGACTCGAAC CTTTTATGGT CTGCATCAGG ACTTCCCCAG CGTGGTGCTA     480

GTTGGCCTCG GCAAAAAGGC AGCTGGAATC GACGAACAGG AAAACTGGCA TGAAGGCAAA     540

GAAAACATCA GAGCTGCTGT TGCAGCGGGG TGCAGGCAGA TTCAAGACCT GGAGCTCTCG     600

TCTGTGGAGG TGGATCCCTG TGGAGACGCT CAGGCTGCTG CGGAGGGAGC GGTGCTTGGT     660

CTCTATGAAT ACGATGACCT AAAGCAAAAA AAGAAGATGG CTGTGTCGGC AAAGCTCTAT     720

GGAAGTGGGG ATCAGGAGGC CTGGCAGAAA GGAGTCCTGT TTGCTTCTGG GCAGAACTTG     780

GCACGCCAAT TGATGGAGAC GCCAGCCAAT GAGATGACGC CAACCAGATT TGCTGAAATT     840

ATTGAGAAGA ATCTCAAAAG TGCTAGTAGT AAAACCGAGG TCCATATCAG ACCCAAGTCT     900

TGGATTGAGG AACAGGCAAT GGGATCATTC CTCAGTGTGG CCAAAGGATC TGACGAGCCC     960

CCAGTCTTCT TGGAAATTCA CTACAAAGGC AGCCCCAATG CAAACGAACC ACCCCTGGTG    1020

TTTGTTGGGA AAGGAATTAC CTTTGACAGT GGTGGTATCT CCATCAAGGC TTCTGCAAAT    1080

ATGGACCTCA TGAGGGCTGA CATGGGAGGA GCTGCAACTA TATGCTCAGC CATCGTGTCT    1140

GCTGCAAAGC TTAATTTGCC CATTAATATT ATAGGTCTGG CCCCTCTTTG TGAAAATATG    1200

CCCAGCGGCA AGGCCAACAA GCCGGGGGAT GTTGTTAGAG CCAAAAACGG GAAGACCATC    1260

CAGGTTGATA CACTGATGC TGAGGGGAGG CTCATACTGG CTGATGCGCT CTGTTACGCA    1320

CACACGTTTA ACCCGAAGGT CATCCTCAAT GCCGCCACCT AACAGGTGC CATGGATGTA    1380

GCTTTGGGAT CAGGTGCCAC TGGGGTCTTT ACCAATTCAT CCTGGCTCTG GAACAAACTC    1440

TTCGAGGCCA GCATTGAAAC AGGGGACCGT GTCTGGAGGA TGCCTCTCTT CGAACATTAT    1500

ACAAGACAGG TTGTAGATTG CCAGCTTGCT GATGTTAACA ACATTGGAAA ATACAGATCT    1560

GCAGGAGCAT GTACAGCTGC AGCATTCCTG AAAGAATTCG TAACTCATCC TAAGTGGGCA    1620

CATTTAGACA TAGCAGGCGT GATGACCAAC AAAGATGAAG TTCCCTATCT ACGGAAAGGC    1680

ATGACTGGGA GGCCCACAAG GACTCTCATT GAGTTCTTAC TTCGTTTCAG TCAAGACAAT    1740

GCTTAGTTCA GATACTCAAA AATGTCTTCA CTCTGTCTTA AATTGGACAG TTGAACTTAA    1800

AAGGTTTTTG AATAAATGGA TGAAATCTT TTAACGGAGA CAAAGGATGG TATTTAAAAA    1860

TGTAGAACAC AATGAAATTT GTATGCCTTG ATTTTTTTTT TCATTTCACA CAAAGATTTA    1920

TAAAGGTAAA GTTAATATCT TACTTGATAA GGATTTTTAA GATACTCTAT AAATGATTAA    1980

AATTTTTAGA ACTTCCTAAT CACTTTTCAG AGTATATGTT TTTCATTGAG AAGCAAAATT    2040
```

```
GTAACTCAGA TTTGTGATGC TAGGAACATG AGCAAACTGA AAATTACTAT GCACTTGTCA    2100

GAAACAATAA ATGCAACTTG TTGTGAAAAA AAAAAA                               2136
```

(2) INFORMATION FOR SEQ ID NO: 22:

(i) SEQUENCE CHARACTERISTICS:
        (A) LENGTH: 1388 base pairs
        (B) TYPE: nucleic acid
        (C) STRANDEDNESS: single
        (D) TOPOLOGY: linear (vii) IMMEDIATE SOURCE:
        (A) LIBRARY: SMCANOT01
        (B) CLONE: 2484218

(xi) SEQUENCE DESCRIPTION: SEQ ID NO: 22 :

```
GGAAAATGGC GGCGGCGGCG GCGGCGGCTG CAGCTACGAA CGGGACCGGA GGAAGCAGCG      60

GGATGGAGGT GGATGCAGCA GTAGTCCCCA GCGTGATGGC CTGCGGAGTG ACTGGGAGTG     120

TTTCCGTCGC TCTCCATCCC CTTGTCATTC TCAACATCTC AGACCACTGG ATCCGCATGC     180

GCTCCCAGGA GGGGCGGCCT GTGCAGGTGA TTGGGCTCT GATTGGCAAG CAGGAGGGCC      240

GAAATATCGA GGTGATGAAC TCCTTTGAGC TGCTGTCCCA CACCGTGGAA GAGAAGATTA     300

TCATTGACAA GGAATATTAT TACACCAAGG AGGAGCAGTT TAAACAGGTG TTCAAGGAGC     360

TGGAGTTTCT GGGTTGGTAT ACCACAGGGG GGCCACCTGA CCCCTCGGAC ATCCACGTCC     420

ATAAGCAGGT GTGTGAGATC ATCGAGAGCC CCCTCTTTCT GAAGTTGAAC CCTATGACCA     480

AGCACACAGA TCTTCCTGTC AGCGTTTTTG AGTCTGTCAT TGATATAATC AATGGAGAGG     540

CCACAATGCT GTTTGCTGAG CTGACCTACA CTCTGGCCAC AGAGGAAGCG GAACGCATTG     600

GTGTAGACCA CGTAGCCCGA ATGACAGCAA CAGGCAGTGG AGAGAACTCC ACTGTGGCTG     660

AACACCTGAT AGCACAGCAC AGCGCCATCA AGATGCTGCA CAGCCGCGTC AAGCTCATCT     720

TGGAGTACGT CAAGGCCTCT GAAGCGGGAG AGGTCCCCTT TAATCATGAG ATCCTGCGGG     780

AGGCCTATGC TCTGTGTCAC TGTCTCCCGG TGCTCAGCAC AGACAAGTTC AAGACAGATT     840

TTTATGATCA ATGCAACGAC GTGGGGCTCA TGGCCTACCT CGGCACCATC ACCAAAAACGT    900

GCAACACCAT GAACCAGTTT GTGAACAAGT TCAATGTCCT CTACGACCGA CAAGGCATCG     960

GCAGGAGAAT GCGCGGGCTC TTTTTCTGAT GAGGGTACTT GAAGGGCTGA TGGACAGGGG    1020

TCAGGCAACT ATCCCAAAGG GGAGGGCACT ACACTTCCTT GAGAGAAACC GCTGTCATTA    1080

ATAAAAGGGG AGCAGCCCCT GAGCACCCCT GCTGGTGGCT CTGTCCTCTG TTAGGCACCA    1140

CACTGGTTGG TCAACTTGGA TGTTCATCGA GGCTCATTCT GGCCTTGCTC AGAAGCCCTT    1200

CTGATGCTCT TCAGTGAGGG AGGCACTACC ATTTGAAGTG ACCCCATGTC AGTCACATGG    1260

ACTGGTCTTT AGCAAAGTCC AAGGCTGCCT GCTTCCACCT AAGTGGTCTC TGTTCTACAC    1320

TTTAATGTCA CCCTCTACAT CATCTTACCT AGCCCACCCA ACCTTATAAA CATGATAATT    1380

GACTACTA                                                              1388
```

(2) INFORMATION FOR SEQ ID NO: 23:

(i) SEQUENCE CHARACTERISTICS:
        (A) LENGTH: 2476 base pairs
        (B) TYPE: nucleic acid
        (C) STRANDEDNESS: single
        (D) TOPOLOGY: linear (vii) IMMEDIATE SOURCE:
        (A) LIBRARY: SINIUCT01
        (B) CLONE: 2680548

(xi) SEQUENCE DESCRIPTION: SEQ ID NO: 23 :

```
CTCGCGTCCT GGGTGCCGCC TCTGAGTAGG GCGGGCGAGG AGGCAGCCAA GGCGGAGCTG      60
ATGGCTGCGC CGAGGGCGGG GCGGGGTGCA GGCTGGAGCC TTCGGGCATG GCGGGCTTTG     120
GGGGGCATTC GCTGGGGGAG GAGACCCCGT TTGACCCCTG ACCTCCGGGC CCTGCTGACG     180
TCAGGAACTT CTGACCCCCG GGCCCGAGTG ACTTATGGGA CCCCCAGTCT CTGGGCCCGG     240
TTGTCTGTTG GGGTCACTGA ACCCCGAGCA TGCCTGACGT CTGGGACCCC GGGTCCCCGG     300
GCACAACTGA CTGCGGTGAC CCCAGATACC AGGACCCGGG AGGCCTCAGA GAACTCTGGA     360
ACCCGTTCGC GCGCGTGGCT GGCGGTGGCG CTGGGCGCTG GGGGGCAGT GCTGTTGTTG      420
TTGTGGGGCG GGGGTCGGGG TCCTCCGGCC GTCCTCGCCG CCGTCCCTAG CCCGCCGCCC     480
GCTTCTCCCC GGAGTCAGTA CAACTTCATC GCAGATGTGG TGGAGAAGAC AGCACCTGCC     540
GTGGTCTATA TCGAGATCCT GGACCGGCAC CCTTTCTTGG GCCGCGAGGT CCCTATCTCG     600
AACGGCTCAG GATTCGTGGT GGCTGCCGAT GGGCTCATTG TCACCAACGC CCATGTGGTG     660
GCTGATCGGC GCAGAGTCCG TGTGAGACTG CTAAGCGGCG ACACGTATGA GGCCGTGGTC     720
ACAGCTGTGG ATCCCGTGGC AGACATCGCA ACGCTGAGGA TTCAGACTAA GGAGCCTCTC     780
CCCACGCTGC CTCTGGGACG CTCAGCTGAT GTCCGGCAAG GGGAGTTTGT TGTTGCCATG     840
GGAAGTCCCT TTGCACTGCA GAACACGATC ACATCCGGCA TTGTTAGCTC TGCTCAGCGT     900
CCAGCCAGAG ACCTGGGACT CCCCCAAACC AATGTGGAAT ACATTCAAAC TGATGCAGCT     960
ATTGATTTTG GAAACTCTGG AGGTCCCCTG GTTAACCTGG ATGGGGAGGT GATTGGAGTG    1020
AACACCATGA AGGTCACAGC TGGAATCTCC TTTGCCATCC CTTCTGATCG TCTTCGAGAG    1080
TTTCTGCATC GTGGGGAAAA GAAGAATTCC TCCTCCGGAA TCAGTGGGTC CCAGCGGCGC    1140
TACATTGGGG TGATGATGCT GACCCTGAGT CCCAGCATCC TTGCTGAACT ACAGCTTCGA    1200
GAACCAAGCT TTCCCGATGT TCAGCATGGT GTACTCATCC ATAAAGTCAT CCTGGGCTCC    1260
CCTGCACACC GGGCTGGTCT GCGGCCTGGT GATGTGATTT TGGCCATTGG GGAGCAGATG    1320
GTACAAAATG CTGAAGATGT TTATGAAGCT GTTCGAACCC AATCCCAGTT GGCAGTGCAG    1380
ATCCGGCGGG GACGAGAAAC ACTGACCTTA TATGTGACCC CTGAGGTCAC AGAATGAATA    1440
GATCACCAAG AGTATGAGGC TCCTGCTCTG ATTTCCTCCT TGCCTTTCTG GCTGAGGTTC    1500
TGAGGGCACC GAGACAGAGG GTTAAATGAA CCAGTGGGGG CAGGTCCCTC CAACCACCAG    1560
CACTGACTCC TGGGCTCTGA AGAATCACAG AAACACTTTT TATATAAAAT AAAATTATAC    1620
CTAGCAACAT ATTATAGTAA AAAATGAGGT GGGAGGGCTG GATCTTTTCC CCCACCAAAA    1680
GGCTAGAGGT AAAGCTGTAT CCCCCTAAAC TTAGGGGAGA TACTGGAGCT GACCATCCTG    1740
ACCTCCTATT AAAGAAAATG AGCTGCTGCC ATCTTTTGTG GGCAGTTAGT CAGGTGCTGC    1800
TCTTTGTGGT GTGGTGGGCT CTGGTCTGTT CTGCTCGGTG CTGGGCCTGG GAGCAAAGAT    1860
TCCCATGCTT GGCTACAGAT ACTGACAGCT GGCCTCTGAA GGAGGGTGAA AACTTCTGCT    1920
TGACAGTTCC ACATCCATAG TGCATGGTCT GATGAGTGCG GTTGCTGACA TGGGTTTCTT    1980
GGTAAGCTCC TGAGGTAATG GCAGCCTCAG ACCCCTGCCA TTAGGGGCCA GTGGTGGTTT    2040
GCAGAGGGCA GTGGCACTTA GATAATCTGG TTGCTGGTCT GGCCAGGGTA GCGTTCAAAC    2100
CTCCTGTTGG CCTCTTCACT GAAGGCATCA CCAATGTGGC AGTTGTGCAC CCAGATTCTA    2160
TGTCCATCAT ATTTGCAGTT ACATTTCATT GCATTGTTGG TAAAGTCACT CTCTGCTACT    2220
TCAAAGTTTG GGTTGATGAC AACCTGGAGA ATGTAGTTTC CTGGCTTCAC ATCCGTGATG    2280
```

-continued

```
TCAATCCACT GACAGTCAAT GTCATGCCGG TAGAGATCCC AGCAACCCAC AGTGATGCCT      2340

TGCTCTCCAA AGTTGGCACA CTCATACCGC TTGGAGACAT CCTCCTGACA CTCAGTGTCT      2400

TCGAGACAGA AACTAGCTTT GTGGCCCTCA GCCACCTTGG TGCCATTTGG GGTGAGGATA      2460

TCATAGTGAG TGAAGA                                                      2476
```

(2) INFORMATION FOR SEQ ID NO: 24:

(i) SEQUENCE CHARACTERISTICS:
        (A) LENGTH: 2231 base pairs
        (B) TYPE: nucleic acid
        (C) STRANDEDNESS: single
        (D) TOPOLOGY: linear (vii) IMMEDIATE SOURCE:
        (A) LIBRARY: KIDNFET01
        (B) CLONE: 2957969

(xi) SEQUENCE DESCRIPTION: SEQ ID NO: 24 :

```
GTTTGAAACA GCTTCACAAG GCTGGTTATG AAGAAGAAAC TCAAAATAAC AGGAGTGGCT        60

TATGGAACTA CATGGAGGTA ACAGAGGAGG GTACCAACCA AAGGCCCTTG AGCAATCAGG       120

ATGTTGGGGG CGTGGGCCGG CAGGAAGATG GCGAACGTGG GGCTGCAGTT CCAGGCGAGC       180

GCGGGGGACT CGGACCCACA GAGCCGGCCC CTGCTGCTGC TCGGGCAGCT GCACCACCTG       240

CACCGCGTGC CCTGGAGCCA CGTCCGCGGG AAGCTGCAGC CCCGGGTCAC CGAGGAGCTC       300

TGGCAGGCTG CCCTGAGCAC GCTCAACCCC AACCCCACGG ACAGCTGTCC CCTCTACCTG       360

AACTACGCCA CCGTGGCTGC CCTGCCCTGC AGGGTGAGCC GGCACAACAG CCCCTCGGCC       420

GCCCACTTCA TCACGCGGCT GGTGCGGACC TGCCTGCCGC CCGGAGCGCA TCGCTGCATT       480

GTGATGGTCT GCGAGCAGCC GGAGGTCTTT GCTTCCGCCT GTGCCCTGGC CCGGGCCTTC       540

CCGCTGTTCA CCCACCGCTC AGGTGCCTCT CGGCGCTTGG AGAAGAAGAC GGTCACCGTG       600

GAGTTTTTCC TGGTGGGACA AGACAACGGG CCGGTGGAGG TGTCCACATT GCAGTGCTTA       660

GCGAATGCCA CAGACGGCGT GCGGCTAGCA GCCCGCATCG TGGACACACC CTGCAATGAG       720

ATGAACACCG ACACCTTCCT CGAGGAGATT AACAAAGTTG AAAGGAGCT GGGGATCATC        780

CCAACCATCA TCCGGGATGA GGAACTGAAG ACGAGAGGAT TTGGAGGAAT CTATGGGGTT       840

GGCAAAGCCG CCCTGCATCC CCCAGCCCTG GCCGTCCTCA GCCACACCCC AGATGGAGCC       900

ACGCAGACCA TCGCCTGGGT GGGCAAAGGC ATCGTCTATG ACACTGGAGG CCTCAGCATC       960

AAAGGGAAGA CTACCATGCC GGGGATGAAG CGAGACTGCG GGGTGCTGC GGCCGTCCTG       1020

GGGGCCTTCA GAGCCGCAAT CAAGCAGGGT TTCAAAGACA ACCTCCACGC TGTGTTCTGC      1080

TTGGCTGAGA ACTCGGTGGG GCCCAATGCG ACAAGGCCAG ATGACATCCA CCTGCTGTAC      1140

TCAGGGAAGA CGGTGGAAAT CAACAACACG GATGCCGAGG GCAGGCTGGT GCTGGCAGAT      1200

GGCGTGTCCT ATGCTTGCAA GGACCTGGGG GCCGACATCA TCCTGGACAT GGCCACCCTG      1260

ACCGGGGCTC AGGGCATTGC CACAGGGAAG TACCACGCCG CGGTGCTCAC CAACAGCGCT      1320

GAGTGGGAGG CCGCCTGTGT GAAGGCGGGC AGGAAGTGTG GGACCTGGT GCACCCGCTG       1380

GTCTACTGCC CCGAGCTGCA CTTCAGCGAG TTCACCTCAG CTGTGGCGGA CATGAAGAAC      1440

TCAGTGGCGG ACCGAGACAA CAGCCCCAGC TCCTGTGCTG GCCTCTTCAT CGCCTCACAC      1500

ATCGGCTTCG ACTGGCCCGG AGTCTGGGTC CACCTGGACA TTGCTGCACC GGTGCATGCT      1560

GGTGAGCGAG CCACAGGCTT CGGTGTGGCC CTCCTGCTGG CGCTCTTCGG CCGTGCCTCT      1620

GAGGACCCTC TGCTGAACCT GGTGTCCCCA CTGGGCTGTG AGGTGGATGT CGAGGAGGGG      1680
```

-continued

| | | | | | |
|---|---|---|---|---|---|
| GACGTGGGGA | GGGACTCCAA | GAGACGCAGG | CTTGTGTGAG | CCTCCTGCCT | CGGCCCTGAC | 1740 |
| AAACGGGGAT | CTTTTACCTC | ACTTTGCACT | GATTAATTTT | AAGCAATTGA | AAGATTGCCC | 1800 |
| TTCATATGGG | TTTTGGTTTG | TCTTTCTGGT | CGTCAGCGTG | GTGGTGGAAA | CAGCTGAAGT | 1860 |
| TTTAGGAGAC | AGCTTAGGGT | TTGGTGCGGG | CCACGGGGAG | GGGACCGGGA | AGCGCTGGGG | 1920 |
| CTTGTTTCTG | TTTGTTACTT | ACAGGACTGA | GACATCTTCT | GTAAACTGCT | ACCCCTGGGG | 1980 |
| CCTTCTGCAC | CCCGGGGTGA | GGCCTCCTGC | CTGCCTGGTG | CCCTGTCCCA | GCCCCAGGTC | 2040 |
| CTGTGCAGGG | CACCTGCGTG | GCTGACAGCC | AGGCTCTTAC | TCCAGCCGGG | GCTGCCAGCG | 2100 |
| CATCCAGCCA | GCCCAGCCCT | GTGAAAGATG | GAGCTGACTT | GCTGCAGGGG | ACCTGATTTA | 2160 |
| TAGGGCAAGA | GAAGTCACAC | TCTGGCCTCT | CAGAATTCAC | TTGAGGTTCA | ATTAAATACA | 2220 |
| GTCACACCGC | C | | | | | 2231 |